(12) United States Patent
Aher et al.

(10) Patent No.: US 9,718,773 B2
(45) Date of Patent: Aug. 1, 2017

(54) SUBSTITUTED 5 MEMBERED HETEROCYCLIC COMPOUNDS AND PREPARATION THEREOF

(71) Applicant: Council of Scientific and Industrial Research, New Delhi (IN)

(72) Inventors: Ravindra Dattatray Aher, Pune (IN); Boopathi Senthil Kumar, Pune (IN); Arumugam Sudalai, Pune (IN); Komal Girdhari Lalwani, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/109,474

(22) PCT Filed: Jan. 5, 2015

(86) PCT No.: PCT/IN2015/000004
§ 371 (c)(1),
(2) Date: Jul. 1, 2016

(87) PCT Pub. No.: WO2015/102024
PCT Pub. Date: Jul. 9, 2015

(65) Prior Publication Data
US 2016/0326110 A1 Nov. 10, 2016

(30) Foreign Application Priority Data

Jan. 3, 2014 (IN) .......................... 0014/DEL/2014
Jan. 21, 2014 (IN) .......................... 0182/DEL/2014
Feb. 14, 2014 (IN) .......................... 0420/DEL/2014

(51) Int. Cl.
*C07D 207/48* (2006.01)
*C07D 231/04* (2006.01)
*C07D 405/06* (2006.01)
*C07D 409/06* (2006.01)
*C07D 498/04* (2006.01)

(52) U.S. Cl.
CPC ......... *C07D 207/48* (2013.01); *C07D 231/04* (2013.01); *C07D 405/06* (2013.01); *C07D 409/06* (2013.01); *C07D 498/04* (2013.01)

(58) Field of Classification Search
CPC .. C07D 207/48; C07D 231/04; C07D 405/06; C07D 409/06; C07D 498/04
See application file for complete search history.

(56) References Cited

U.S. PATENT DOCUMENTS

| 4,691,022 A | 9/1987 | Henning et al. |
| 4,988,710 A | 1/1991 | Olney |
| 2003/0114666 A1 | 6/2003 | Ellsworth |

FOREIGN PATENT DOCUMENTS

| EP | 0132580 A1 | 2/1985 |
| WO | WO-2015102024 | 7/2015 |

OTHER PUBLICATIONS

"International Application No. PCT/IN2015/000004, International Search Report and Written Opinion mailed Aug. 4, 2015", (Aug. 4, 2015), 17 pgs.
Aher, Ravindra D., et al., "Proline-Catalyzed Sequential *syn*-Mannich and [4+1]-Annulation Cascade Reactions to Form Densely Functionalized Pyrrolidines", *J. Org. Chem.*, 80(3), (2015), 2024-2031.
Kontinen, Vesa K., et al., "Vocalization Responses After Intrathecal Administration of Ionotropic Glutamate Receptor Agonists in Rats", *Anesthesia & Analgesia*, 95(4), (Oct. 2002), 997-1001.
Kumar, B. Senthil, et al., "Organocatalytic Sequential α-Amination/Corey-Chaykovsky Reaction of Aldehydes: A High Yield Synthesis of 4-Hydroxypyrazolidine Derivatives", *Org. Lett.*, 14(10), (2012), 2468-2471.
Kumar, Vivek, et al., "Identification of hotspot regions of MurB oxidoreductase enzyme using homology modeling, molecular dynamics and molecular docking techniques". *Journal of Molecular Modeling*, 17(5), (May 2011), 939-953.
Lalwani, Komal G., et al., "Organocatalytic [4+1]-annulation approach for the synthesis of densely functionalized pyrazolidine carboxylates", *RSC Advances*, 5, (2015), 65554-65559.
Presset, Marc, et al., "1,3-Dipolar Cycloaddition of Hydrazones with α-Oxo-ketenes: A Three-Component Stereoselective Entry to Pyrazolidinones and an Original Class of Spirooxindoles", *Org. Lett.*, 13(15), (2011), 4124-4127.

*Primary Examiner* — Kahsay Habte
(74) *Attorney, Agent, or Firm* — Schwegman Lundberg & Woessner, P.A.

(57) ABSTRACT

Novel substituted 5 membered heterocyclic compounds of Formula I are disclosed. The invention further discloses a process for the preparation of compounds of Formula I. The compounds find use as anti mycobacterial agents.

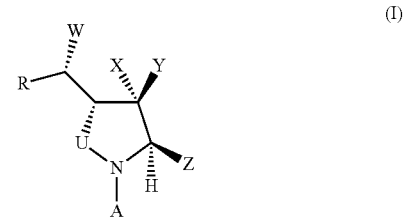

7 Claims, 4 Drawing Sheets

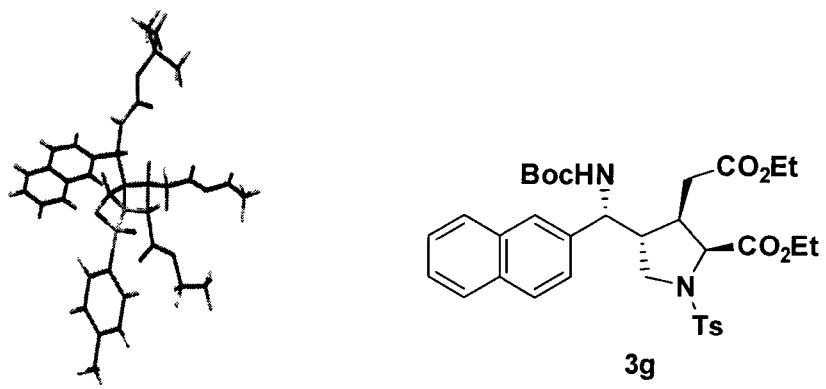
Fig: 1
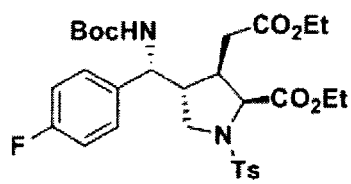
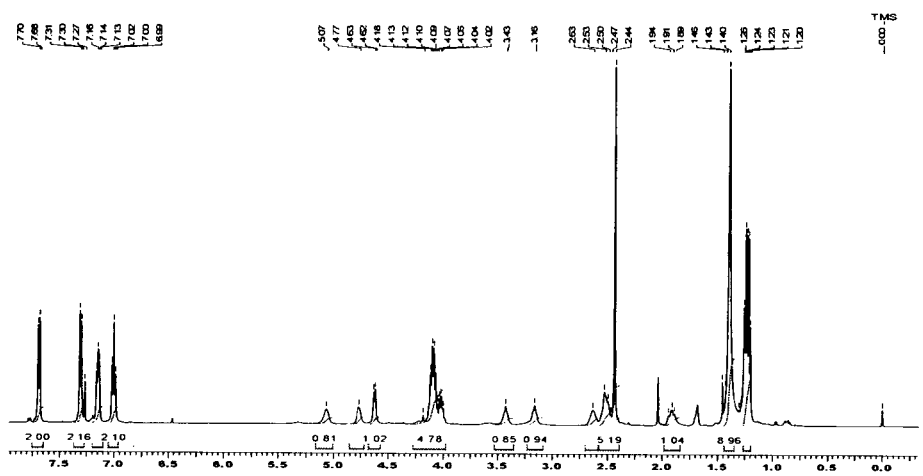
Fig: 2

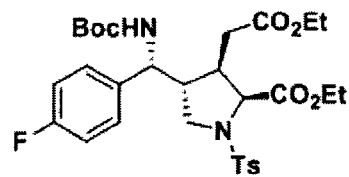
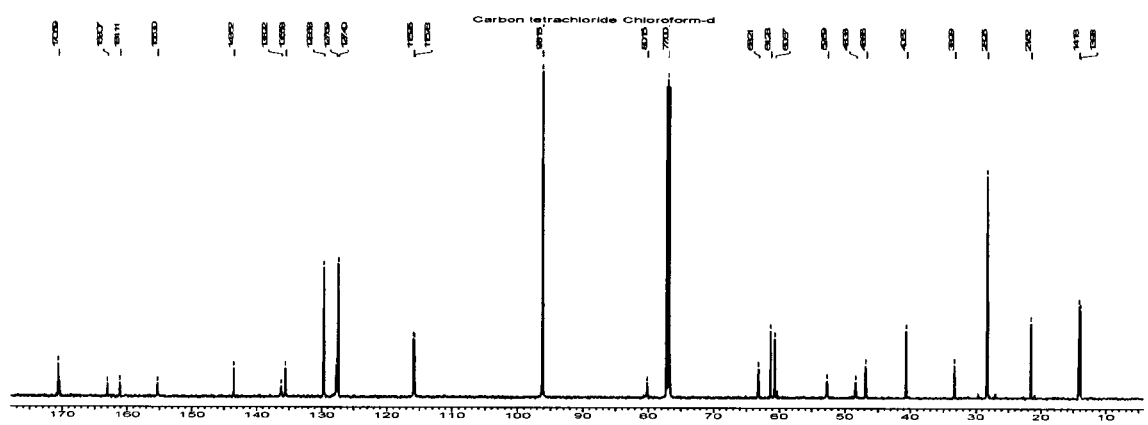
Fig: 3
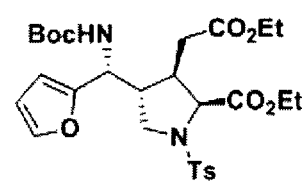
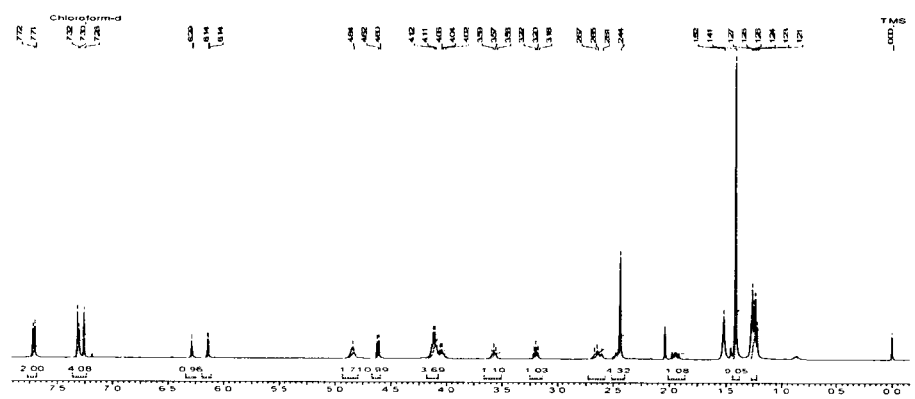
Fig: 4

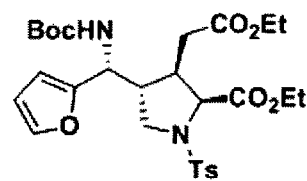
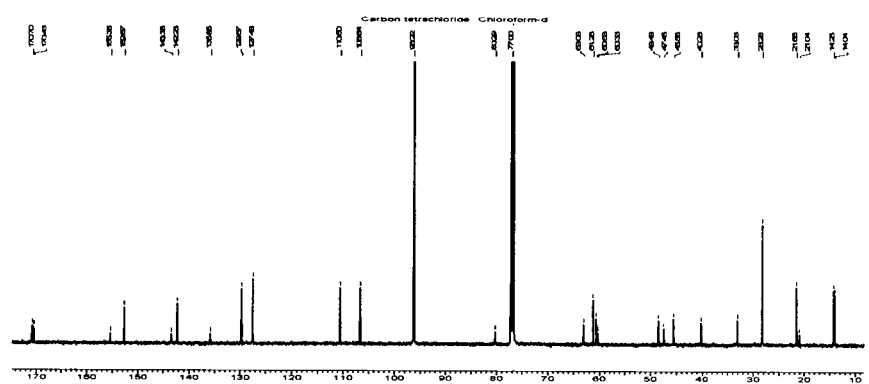
Fig: 5
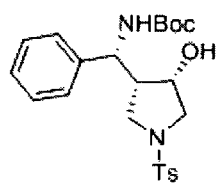
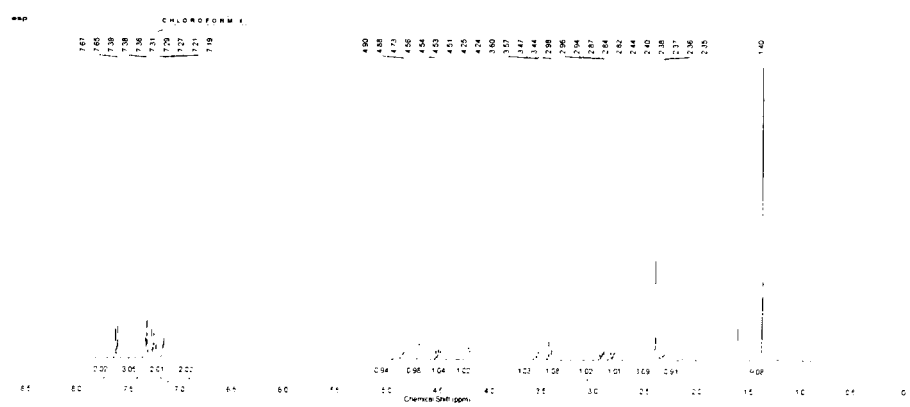
Fig: 6

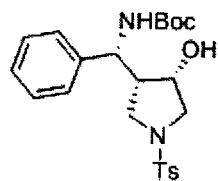
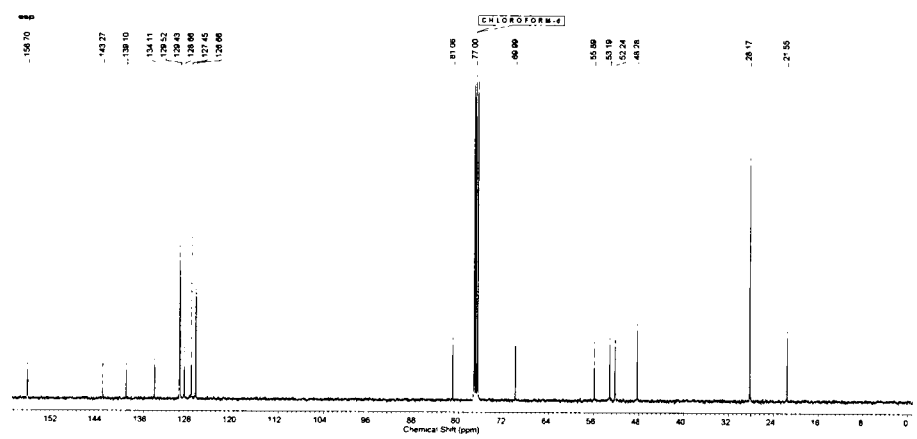
Fig: 7
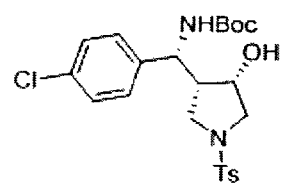
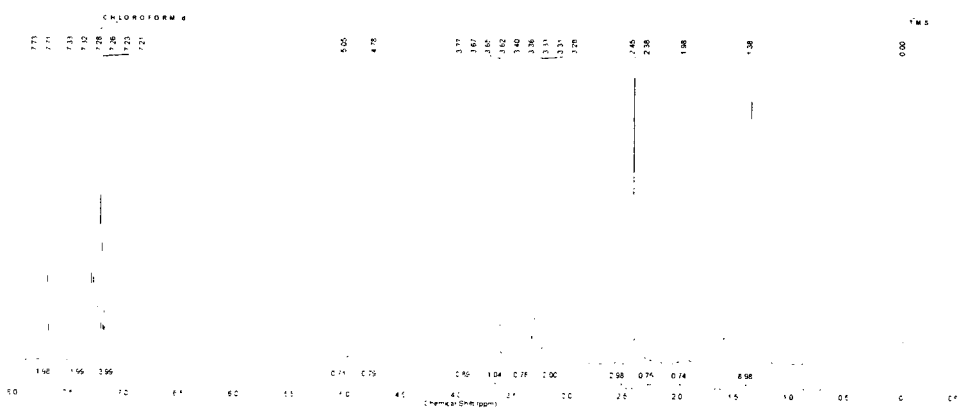
Fig.8

SUBSTITUTED 5 MEMBERED HETEROCYCLIC COMPOUNDS AND PREPARATION THEREOF

PRIORITY CLAIM TO RELATED APPLICATIONS

This application is a U.S. national stage application filed under 35 U.S.C. §371 from International Application Serial No. PCT/IN2015/000004, which was filed 05 Jan. 2015, and published as WO2015/102024 on 09 Jul. 2015, and which claims priority to Indian Application No. 0014/DEL/2014, filed 03 Jan. 2014, and which claims priority to Indian Application No. 0182/DEL/2014, filed 21 Jan. 2014, and which claims priority to Indian Application No. 0420/DEL/2014, filed 14 Feb. 2014, which applications and publication are incorporated by reference as if reproduced herein and made a part hereof in their entirety, and the benefit of priority of each of which is claimed herein.

FIELD OF THE INVENTION

The present invention relates to a novel substituted 5 membered heterocyclic compounds. Further, the invention provides a novel process for synthesis of a 5 membered heterocyclic compounds and their enantiomers. The compounds find use as anti tubercular agents.

BACKGROUND AND PRIOR ART

The derivatives of functionalized pyrrolidines are structural components of many bioactive natural products and pharmaceutically important substances. In particular, anisomycin is a basic antibiotic, while domoic acid and kainic acid are potent neuroexcitatory amino acids.

EP 0132580 A1 reports a process for the preparation of a compound of formula I,

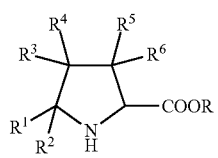

in which R is hydrogen, ($C_1$-$C_6$) alkyl or ($C_7$-$C_9$) aralkyl group, and $R^1$ to $R^6$ are identical or different and are independently hydrogen, ($C_1$-$C_8$)-alkyl, ($C_3$-$C_9$)-cycloalkyl, ($C_3$-$C_9$) cycloalkyl ($C_1$-$C_4$) alkyl, ($C_5$-$C_9$) cycloalkenyl ($C_1$-$C_4$) alkyl, ($C_6$-$C_{12}$)-aryl-($C_1$-$C_4$) alkyl or ($C_6$-$C_{12}$)-aryl, in each case both in the aryl moiety by ($C_1$-$C_4$)-alkyl, ($C_1$-$C_4$) alkoxy, hydroxy, halogen, nitro, methylenedioxy and/or cyano, mono-, di- or tri-substituted can be mean, or in which two of the radicals R to $R^6$, together with the carbon atom carrying or: with the two carrying them, carbon atoms, a 4- to 10-membered saturated or unsaturated mono- or bicyclic carbocyclic ring system and the other radicals are hydrogen, characterized in that a pyrrolidine derivative of the formula II,

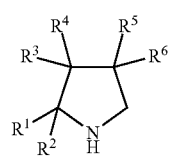

in which $R^1$ to $R^6$ have the same meaning as in formula I, with an oxidizing agent in the presence of a silver salt in a $\Delta^1$-Pyrrolinderivat of the formula III,

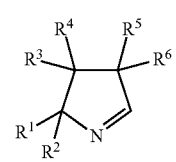

in which R and $R^6$ have the same meaning as in formula I, transferred, this, with hydrogen cyanide or a metal cyanide to give a compound of the formula IV,

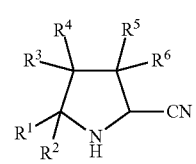

in which $R^1$ to $R^6$ have the same meaning as in formula I, is reacted, and with a compound of the formula ROH in which R has the meaning defined above, are reacted to form a compound of the formula I.

U.S. Pat. No. 4,988,710 reports

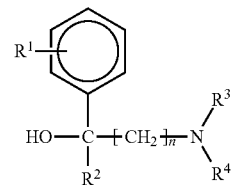

wherein R1 is one or more groups independently selected from hydrido, halo, alkyl, acyl, hydroxyalkyl, haloalkyl, aminoalkyl, alkoxy, amino, alkylamino and acylamino; wherein R2 is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycyclo-alkyl, aminocycloalkyl, bicycloalkyl, bicycloalkenyl and tricycloalkyl wherein the tricycloalkyl, bicyclo-alkenyl and tricycloalkyl groups may be substituted with one or more groups selected from alkyl, halo, acyl, hydroxy, hydroxyalkyl, haloalkyl, acyl, alkoxy, amino and alkylamino; wherein each of R3 and R4 is independently selected from hydrido, alkyl, acyl, alkenyl, cycloalkyl, phenylalkyl, phenyl, aminoalkyl and alkylaminoalkyl; and wherein R3 and R4 may be taken together to form a cyclic group including the nitrogen atom of Formula I, and n is an integer selected from one through five.

Article titled, "1,3-Dipolar Cycloaddition of Hydrazones with α-Oxo-ketenes: A Three-Component Stereoselective Entry to Pyrazolidinones and an Original Class of Spirooxindoles" by Marc Presset; Kishor Mohanan; Marie Hamann; Yoann Coquerrel; Jean Rodriguez. in Org. Lett. 2011, 13, 4124 reports stereodefined monocyclic, spirobicyclic, and bis-spirotricyclic pyrazolidin-3-ones efficient preparation by a three-component reaction involving a 1,3-dipolar cycloaddition of azomethine imines obtained from hydrazones with α-oxo-ketene dipolarophiles generated in situ, with excellent diastereoselectivity in a single catalyst/additive-free, highly economic transformation.

Article titled, "Organocatalytic Sequential α-Amination/Corey-Chaykovsky Reaction of Aldehydes: A High Yield Synthesis of 4-Hydroxypyrazolidine Derivatives" by B. Senthil Kumar; V. Venkatramasubramanian; Arumugam Sudalai. in Org. Lett. 2012, 14, 2468 reports a tandem reaction of in situ generated α-amino aldehydes with dimethyloxo sulfonium. methylide under Corey-Chaykovsky reaction conditions proceeds efficiently to give 4-hydroxy-pyrazolidine derivatives in high yields with excellent enantio- and diastereoselectivity. This organocatalytic sequential method provides for the efficient synthesis of anti-1, 2-aminoalcohols, structural subunits present in several bioactive molecules as well.

Above methods involve drawbacks of multistep processes, complex starting materials, expensive as well as toxic transition metal catalysis, poor enantio and diastereoselectivity. Our method overcomes these shortages through very good enantio and diastereoselectivity with good yields in a one-pot process via organocatalysis.

Due to their biological importance and structural complexity, easy and efficient method of construction of pyrrolidine units is the need of time.

OBJECTIVE OF THE INVENTION

The main object of the present invention is to provide a novel substituted 5 membered heterocyclic compounds and its preparation thereof.

SUMMARY OF THE INVENTION

Accordingly, the present invention provides a novel substituted 5 membered heterocyclic compounds of Formula I and its enantiomers,

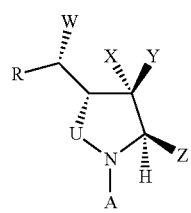

I wherein,
i) when, U is CH$_2$ then A is Ts; W is NHBoc; R is aryl, substituted aryl or heteroaryl; and
  a) X is OH, Y and Z are Hydrogen; or
  b) X is H, Y is —CH$_2$COOEt and Z is —COOEt.
ii) when, U is NCOOR' then A is COOR'; W is H; R is H, aryl, substituted aryl, alkyl, substituted, linear or branched alkyl; X is —CH$_2$COOEt; Y is H; Z is H and R' is alkyl-linear or branched, In an embodiment, a novel process for synthesis of compounds of Formula I and enantiomers of the compounds of Formula I is disclosed.

In a preferred embodiment, the process provides yield of compounds of Formula I in the range of 60-80%.

In another preferred embodiment, the process provides compounds of Formula I and its enantiomers with ee in the range of 80-100%.

In an aspect of the invention, the compounds of Formula I inhibit mycobacteria.

BRIEF DESCRIPTION OF THE DRAWINGS

FIG. 1 depicts X-Ray Crystal structure of ethyl (2S,3R, 4R)-4-((R)-((tert-butoxycarbonyl)amino)(naphthalen-2-yl) methyl)-3-(2-ethoxy-2-oxoethyl)-1-tosylpyrrolidine-2-carboxylate.

FIG. 2 depicts $^1$H NMR spectra of ethyl (2S,3R,4R)-4-((R)-((tert-butoxycarbonyl)amino)(4-fluorophenyl)methyl)-3-(2-ethoxy-2-oxoethyl)-1-tosylpyrrolidine-2-carboxylate (IB).

FIG. 3 depicts $^{13}$C NMR spectra of ethyl (2S,3R,4R)-4-((R)-((tert-butoxycarbonyl)amino)(4-fluorophenyl)methyl)-3-(2-ethoxy-2-oxoethyl)-1-tosylpyrrolidine-2-carboxylate (IB).

FIG. 4 depicts $^1$H NMR spectra of ethyl (2S,3R,4R)-4-((R)-((tert-butoxycarbonyl)amino)(furan-2-yl)methyl)-3-(2-ethoxy-2-oxoethyl)-1-tosylpyrrolidine-2-carboxylate (IH).

FIG. 5 depicts $^{13}$C NMR spectra of ethyl (2S,3R,4R)-4-((R)-((tert-butoxycarbonyl)amino)(furan-2-yl)methyl)-3-(2-ethoxy-2-oxoethyl)-1-tosylpyrrolidine-2-carboxylate (IH)

FIG. 6 depicts $^1$H NMR Spectra of tert-butyl ((R)-((3R, 4S)-4-hydroxy-1-tosylpyrrolidin-3-yl)(phenyl)methyl)carbamate (Ia).

FIG. 7 depicts $^{13}$C NMR Spectra of tert-butyl ((R)-((3R, 4S)-4-hydroxy-1-tosylpyrrolidin-3-yl)(phenyl)methyl)carbamate (Ia).

FIG. 8 depicts $^1$H NMR Spectra of tert-butyl ((R)-(4-chlorophenyl)((3R,4S)-4-hydroxy-1-tosylpyrrolidin-3-yl) methyl)carbamate (Ib).

DETAILED DESCRIPTION OF THE INVENTION

The invention will now be described in detail in connection with certain preferred and optional embodiments, so that various aspects thereof may be more fully understood and appreciated.

In view of the above, the present invention provides a novel substituted 5 membered heterocyclic compounds and its preparation thereof.

In an embodiment the present invention provides a novel substituted 5 membered heterocyclic compounds of Formula I and its enantiomers,

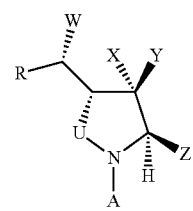

I wherein,
i) when, U is CH$_2$ then A is Ts; W is NHBoc; R is aryl, substituted aryl or heteroaryl; and
   c) X is OH, Y and Z are Hydrogen; or
   d) X is H, Y is —CH$_2$COOEt and Z is —COOEt.
ii) when, U is NCOOR' then A is COOR'; W is H; R is H, aryl, substituted aryl, alkyl, substituted, linear or branched alkyl; X is —CH$_2$COOEt; Y is H; Z is H and R' is alkyl-linear or branched, In an embodiment, the compounds of Formula I and its enantiomers is disclosed.

In another embodiment the present invention provides a process for the synthesis of a novel substituted 5 membered heterocyclic compounds of Formula I, with >98% ee and with >60% yield, wherein the said process comprises the steps of:
a. dissolving N-Boc-protected imine IIa-k in anhydrous acetonitrile and adding the β-amino aldehyde III to obtain a mixture;
b. cooling the mixture of step (a) and adding -proline followed by addition of ethyl 2-(triphenyl-15-phosphanylidene)acetate, ethyl bromo acetate, Cs$_2$CO$_3$ and heating the reaction mixture;
c. cooling the mixture of step (a) and adding proline followed by addition of a solution of CH$_2$=SOMe$_2$ in DMSO/THF; and
d. quenching and work-up of the reaction mixture of step (b) or step (c) affords a pure product IA-H or Ia-k.

In an embodiment the present invention provides a process for the synthesis of a novel substituted 5 membered heterocyclic compounds of Formula I, with >80% ee.

In an embodiment, the proline in the process for the synthesis of compounds of Formula I is L-proline.

In another embodiment, the proline in the process for the synthesis of compounds of Formula I is D-proline.

In a preferred embodiment the present invention provides a process for the synthesis of a novel substituted 5 membered heterocyclic compounds of Formula I, wherein the yield is preferably >65% and more preferably in the range of 65 to 75%.

The above process is shown below in Scheme 1:

Scheme: 1

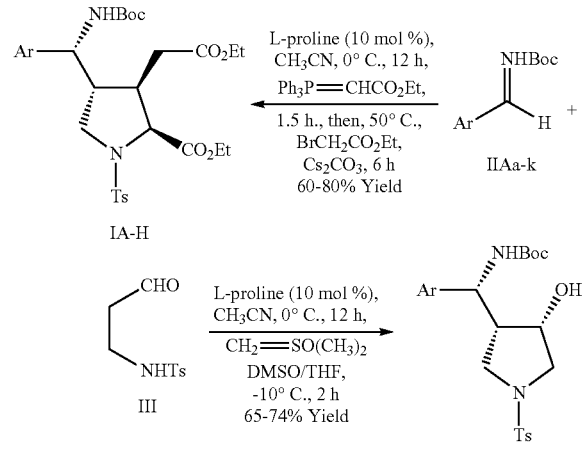

In yet another embodiment the present invention provides a process for the synthesis of a novel substituted 5 membered heterocyclic compounds of Formula 2a to 2m from aldehydes of Formula IVa' to IVj' comprising:
a. adding aldehyde of Formula IVa' to IVj' to a solution of diisopropyl azodicarboxylate (DIAD) and -proline (10 mol %) in CH$_3$CN and stirring to obtain a mixture;
b. adding ethyl 2-(triphenyl-15-phosphanylidene) acetate to the mixture of step (a) and stirring the reaction mixture followed by addition of Corey-Chaykovsky reagent to complete the reaction; and
c. quenching followed by workup affords the pure products 2a to 2m.

The above process is shown below in Scheme 2:

Scheme: 2

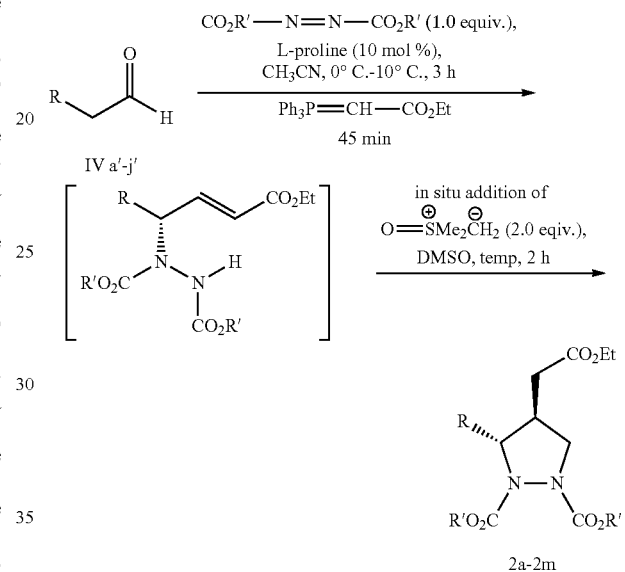

wherein, R is selected from alkyl, linear or branched alkyl substituted other than H, HX or aryl, substituted aryl; and R' is alkyl-linear or branched,

| No. | Substrates IV a'-h' (R) | Amine (R') | Products 2a-2m Yield (%) | ee (%) |
|---|---|---|---|---|
| 1. | Benzyl (IV a') | iPr | 80 | 94 |
| 2 | Benzyl (IV a') | Et | 82 | 92 |
| 3. | Benzyl (IV a') | $^t$Bu | 70 | 90 |
| 4. | Naphthalene-1-yl-methyl (IV b') | iPr | 68 | 86 |
| 5. | 4-methoxybenzyl (IV c') | iPr | 67 | 85 |
| 6. | 3-benzyloxypropyl (IV d') | iPr | 65 | 88 |
| 7. | 4-(methylthio)benzyl (IV e') | iPr | 75 | 93 |
| 8. | 4-methylbenzyl (IV f') | iPr | 71 | 85 |
| 9. | 2-NO$_2$-4,5-methylenedioxybenzyl (IV g') | iPr | 69 | 85 |
| 10. | 2-NO$_2$-4,5-methylenedioxybenzyl (IV g') | $^t$Bu | 63 | 82 |
| 11. | 2-CN-4,5-methylenedioxybenzyl (IV h') | iPr | 65 | 83 |
| 12. | Methyl (IV i') | iPr | 70 | 86 |
| 13. | Propyl (IV j') | iPr | 79 | 87 |

In a preferred embodiment the present invention provides a one pot process for the synthesis of a novel substituted 5 membered heterocyclic compounds of Formula 2a-2m from aldehydes of Formula IVa' to IVj' wherein the yield is >60% (60-85%) with >98% (80-100) ee and >99% dr.

In an aspect the present invention provides compound of Formula Ia-k selected from the following: tert-butyl ((R)-((3R,4S)-4-hydroxy-1-tosylpyrrolidin-3-yl)(phenyl)methyl) carbamate (Ia); tert-butyl ((R)-(4-chlorophenyl)((3R,4S)-4-hydroxy-1-tosylpyrrolidin-3-yl)methyl)carbamate (Ib); tert-butyl ((R)-((3R,4S)-4-hydroxy-1-tosylpyrrolidin-3-yl)(4-(trifluoromethyl)phenyl)methyl)carbamate (Ic); tert-butyl ((R)-((3R,4S)-4-hydroxy-1-tosylpyrrolidin-3-yl)(p-tolyl) methyl)carbamate (Id); (4R,4aR,7aS)-4-(naphthalen-2-yl)-6-tosylhexahydropyrrolo[3,4-e][1,3]oxazin-2(3H)-one (Ie); (4R, 4aR, 7aS)-4-(4-Bromophenyl)-6-tosylhexahydropyrrolo [3,4-e][1,3]oxazin-2(3H)-one (If); 4R, 4aR, 7aS)-4-(4-Fluorophenyl)-6-tosylhexahydropyrrolo [3, 4-e][1,3]oxazin-2(3H)-one (Ig); tert-Butyl ((R)-furan-2-yl((3R, 4S)-4-hydroxy-1-tosylpyrrolidin-3-yl) methyl) carbamate (Ih); tert-Butyl ((R)-((3R, 4S)-4-hydroxy-1-tosylpyrrolidin-3-yl) (4-(methylthio) phenyl)methyl)carbamate (Ii); tert-Butyl ((R)-((3R, 4S)-4-hydroxy-1-tosylpyrrolidin-3-yl)(thiophen-2-yl)methyl) carbamate (Ij); tert-Butyl((R)-((3R, 4S)-4-hydroxy-1-tosylpyrrolidin-3-yl)(4-methoxyphenyl) methyl) carbamate (Ik).

In another aspect the present invention provides compound of Formula IA-H selected from the following: ethyl (2S,3R,4R)-4-((R)-((tert-butoxycarbonyl)amino)(phenyl) methyl)-3-(2-ethoxy-2-oxoethyl)-1-tosylpyrrolidine-2-carboxylate (IA); ethyl (2S,3R,4R)-4-((R)-((tert-butoxycarbonyl)amino)(4-chlorophenyl)methyl)-3-(2-ethoxy-2-oxoethyl)-1-tosylpyrrolidine-2-carboxylate (IB); ethyl (2S, 3R,4R)-4-((R)-((tert-butoxycarbonyl)amino)(4 (trifluoromethyl)phenyl)methyl)-3-(2-ethoxy-2-oxoethyl)-1-tosylpyrrolidine-2-carboxylate (IC); ethyl (2S,3R,4R)-4-((R)-((tert-butoxycarbonyl)amino)(p-tolyl)methyl)-3-(2-ethoxy-2-oxoethyl)-1-tosylpyrrolidine-2-carboxylate (ID); ethyl (2S,3R,4R)-4-((R)-((tert-butoxycarbonyl)amino) (naphthalen-2-yl)methyl)-3-(2ethoxy-2-oxoethyl)-1-tosylpyrrolidine-2-carboxylate (IE); ethyl (2S,3R,4R)-4-((R)-(4-bromophenyl)((tert-butoxycarbonyl)amino)methyl)-3-(2ethoxy-2-oxoethyl)-1-tosylpyrrolidine-2-carboxylate (IF); ethyl (2S,3R,4R)-4-((R)-((tert-butoxycarbonyl)amino)(4-fluorophenyl)methyl)-3-(2ethoxy-2-oxoethyl)-1-tosylpyrrolidine-2-carboxylate (IG); ethyl (2S,3R,4R)-4-((R)-((tert-butoxycarbonyl)amino)(furan-2-yl)methyl)-3-(2-ethoxy-2-oxoethyl)-1-tosylpyrrolidine-2-carboxylate (IH).

In aspect the present invention provides compound of Formula 2a-2m selected from the following: Diisopropyl (3R, 4S)-3-benzyl-4-(2-ethoxy-2-oxoethyl)pyrazolidine-1, 2-dicarboxylate (2a) Diethyl (3R, 4S)-3-benzyl-4-(2-ethoxy-2-oxoethyl) pyrazolidine-1,2-dicarboxylate (2b) Di-tert-butyl (3R,4S)-3-benzyl-4-(2-ethoxy-2-oxoethyl) pyrazolidine-1,2-dicarboxylate (2c) diisopropyl (3R,4S)-4-(2-ethoxy-2-oxoethyl)-3-(naphthalen-2-ylmethyl) pyrazolidine-1,2-dicarboxylate (2d) Diisopropyl (3R,4S)-4-(2-ethoxy-2-oxoethyl)-3-(4-methoxybenzyl)pyrazolidine-1, 2-dicarboxylate (2e) diisopropyl (3R,4S)-3-(3-(benzyloxy) propyl)-4-(2-ethoxy-2-oxoethyl)pyrazolidine-1,2-dicarboxylate (2f) Diisopropyl (3R,4S)-4-(2-ethoxy-2-oxoethyl)-3-(4-(methylthio)benzyl)pyrazolidine-1,2-dicarboxylate (2g) Diisopropyl (3R,4S)-4-(2-ethoxy-2-oxoethyl)-3-(4-methylbenzyl)pyrazolidine-1,2-dicarboxylate (2h) Diisopropyl (3R,4S)-4-(2-ethoxy-2-oxoethyl)-3-((6-nitrobenzo[d][1,3]dioxol-5-yl)methyl) pyrazolidine-1,2-dicarboxylate (2i) di-tert-butyl (3R,4S)-4-(2-ethoxy-2-oxoethyl)-3-((6-nitrobenzo[d][1,3]dioxol-5-yl) methyl)pyrazolidine-1,2-dicarboxylate (2j) Diisopropyl (3R,4S)-3-((6-cyanobenzo[d][1,3]dioxol-5-yl)methyl)-4-(2-ethoxy-2-oxoethyl)pyrazolidine-1,2-dicarboxylate (2k) Diisopropyl (3R,4S)-4-(2-ethoxy-2-oxoethyl)-3-methyl-pyrazolidine-1,2-dicarboxylate (2l) Diisopropyl (3R,4S)-4-(2-ethoxy-2-oxoethyl)-3-propylpyrazolidine-1,2-dicarboxylate (2m)

The compounds of the invention are structurally similar to bioactive natural products containing densely substituted pyrrolidine units such as anisomycin, a basic antibiotic, while domoic acid and kainic acid are potent neuroexcitatory amino acids, and will be expected to possess similar therapeutic activities.

In an embodiment, the compounds of Formula I possess anti mycobcaterial activity. The compound of Formula I is used for the preparation of a pharmaceutical composition in an amount that is therapeutically effective to control a mycobacterial infection.

The pharmaceutical composition may be administered by routes selected from, but not limited to oral, dermal, parenteral, buccal and such like. The composition may be presented in conventional pharmaceutical dosage forms such as tablets, capsules, sachets, granules, patches or injections or as sustained, controlled, delayed, pulsatile or timed release dosage forms.

In another embodiment, the invention discloses a method of treating a subject in need of anti mycobcaterial activity control comprising the compound of formula I.

ADVANTAGES OF INVENTION

1. Novel Synthetic route at industrial scale
2. Product with high optical purities which increases efficiency
3. Experiments done at ambient conditions make the production cheaper.
4. Compounds posses anti mycobacterial activity.

The following examples, which include preferred embodiments, will serve to illustrate the practice of this invention, it being understood that the particulars shown are by way of example and for purpose of illustrative discussion of preferred embodiments of the invention.

EXAMPLES

1. General Information
    Imines IIa-k and β-amino aldehyde III were freshly prepare prior to use following reported methods.
2. Experimental Section
General Experimental Procedure:
    (a) Preparation of sulfurylide:
90 mg (3.75 mmol) of NaH (previously washed with petroleum ether to remove oil) was taken in an oven-dried three-necked flask, followed by the addition of dry DMSO/THF (5 mL each) through a septum to it and the whole slurry was stirred at 25° C. under $N_2$ atmosphere. Then trimethyloxosulfonium iodide (835 mg, 3.75 mmol) was added to the slurry over a period of 5 min via a solid addition funnel until it becomes a homogenous solution.
    (b) Sequential syn-Mannich/Corey-Chaykovsky Reaction:
To a cooled solution of N-Boc imines (IIa-k, 2.5 mmol) and L-proline (10 mol %) in dry $CH_3CN$ (20 mL) at 0° C. was added β-amino aldehyde III (568 mg, 2.75 mmol), and the mixture was stirred for 8-12 h at 0° C. This was followed by the addition of a solution of dimethyloxosulfonium-methylide in DMSO/THF (3.75 mmol) at −10° C. and allowed to stir for 2 h at the same temperature. The progress of the reaction can be monitored by TLC. It was then quenched by the addition of aq. $NH_4Cl$ solution. The mixture was concentrated in vacuum to remove acetonitrile and concentrate extracted with EtOAc (3×30 mL). The combined organic layers were washed with brine, dried over anhyd. Na₂SO₄, and concentrated under reduced pressure to give the crude products, which were then purified by silica gel column chromatography (230-400 mesh) using petroleum ether and ethyl acetate as eluents to afford the pure products Ia-k.

(c) Sequential syn-Mannich/Wittig olefination/N-alkylation/Michael Addition:

To a cooled solution of N-Boc imines (IIa-h, 2.5 mmol) and L-proline (10 mol %) in dry $CH_3CN$ (20 mL) at 0° C. was added β-amino aldehyde III (568 mg, 2.75 mmol), and the mixture was stirred for 8-12 h at 0° C. This was followed by the addition of a ethyl 2-(triphenyl-☐⁵-phosphanylidene)acetate (1.306 g, 3.75 mmol) at 0° C. and allowed to stir for 2 h at the same temperature, it was then added bromoethylacetate (501 mg, 3.455 mL, 3 mmol) and $Cs_2CO_3$ (2.037 g, 6.25 mmol) and the reaction temperature raised to 50° C. and reaction allowed to stir for 6 to 8 h at the same temperature. The progress of the reaction can be monitored by TLC. It was then quenched by the addition of an aq. $NH_4Cl$ solution. The mixture was then extracted with EtOAc (3×30 mL). The combined organic layers were washed with brine, dried over anhyd. $Na_2SO_4$, and concentrated under reduced pressure to give the crude products, which were then purified by flash silica gel column chromatography (230-400 mesh) using petroleum ether and ethyl acetate as eluents to afford the pure products IA-H.

Example 1 tert-butyl ((R)-((3R,4S)-4-hydroxy-1-tosylpyrrolidin-3-yl)(phenyl)methyl)carbamate (Ia)

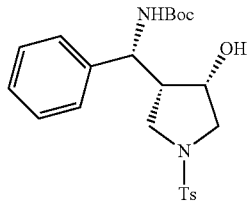 [SMILES: Cc1ccc(S(=O)(=O)N2C[C@H]([C@@H](NC(=O)OC(C)(C)C)c3ccccc3)[C@H](O)C2)cc1]

Yield: 807 mg, 72%; colorless solid; mp: 197-200° C.; $[\alpha]^D_{25}$+10.4 (c 0.2, $CHCl_3$); 99% ee (ChiracelOD-H (250× 4.6 mm), n-Hexane:i-PrOH, 80:20, 0.5 mL/min, 254 nm), $t_r$=11.3 min (minor), $t_r$=10.1 min (major); IR ($CHCl_3$, cm$^{-1}$): $\upsilon_{max}$ 763, 1014, 1296, 1418, 1575, 1652, 1669, 1720, 2917, 3366; $^1$H NMR (400 MHz, $CDCl_3$) δ: 1.40 (s, 9H), 2.35-2.40 (m, 1H), 2.44 (s, 3H), 2.84 (t, J=11.5 Hz, 1H), 2.96 (t, J=8.8 Hz, 1H), 3.44 (d, J=11.5 Hz, 1H), 3.57 (d, J=11.5 Hz, 1H), 4.24 (br s, 1H), 4.53 (dd, J=8.1, 10.8 Hz, 1H), 4.73 (brs, 1H), 4.88 (d, J=7.8 Hz, 1H), 7.19 (d, J=7.3 Hz, 2H), 7.29 (d, J=8.1 Hz, 2H), 7.35-7.40 (m, 3H), 7.65 (d, J=8.1 Hz, 2H); $^{13}$C NMR (100 MHz, $CDCl_3$) δ: 21.5, 28.2 (3), 48.3, 52.2, 53.2, 55.9, 69.9, 81.1, 126.7 (2), 127.4 (2), 128.7, 129.4, 129.5, 134.1, 139.1, 143.3, 156.7; HRMS (ESI) calcd for $C_{23}H_{30}N_2O_5S$ [M+Na]⁺469.1772. found 469.1761.

Example 2 tert-butyl ((R)-(4-chlorophenyl)((3R,4S)-4-hydroxy-1-tosylpyrrolidin-3-yl)methyl)carbamate (Ib)

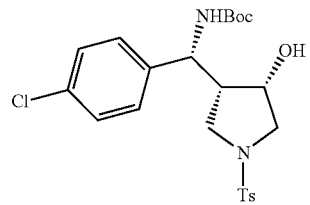 [SMILES: Cc1ccc(S(=O)(=O)N2C[C@H]([C@@H](NC(=O)OC(C)(C)C)c3ccc(Cl)cc3)[C@H](O)C2)cc1]

Yield: 800 mg, 66%; colorless solid; mp:203-205° C.; $[\alpha]^D_{25}$+15.4 (c 0.2, $CHCl_3$); 96% ee (ChiracelOD-H (250× 4.6 mm), n-Hexane:i-PrOH, 80:20, 0.5 mL/min, 254 nm), $t_r$=15.1 min (minor), $t_r$=12.5 min (major); IR ($CHCl_3$, cm$^{-1}$): $\upsilon_{max}$ 1089, 1158, 1317, 1390, 1696; $^1$H NMR (400 MHz, $CDCl_3$) δ: 1.38 (s, 9H), 1.98 (s, 1H), 2.38 (brs, 1H), 2.45 (s, 3H), 3.28 (s, 1H), 3.33 (t, J=10.0 Hz, 1H), 3.40 (s, 1H), 3.65 (t, J=8.8 Hz, 1H), 3.77 (s, 1H), 4.78 (s, 1H), 5.0 (s, 1H), 7.23 (dd, J=8.2, 8.0 Hz, 4H), 7.32 (d, J=7.8 Hz, 2H), 7.71 (d, J=7.8 Hz, 2H); $^{13}$C NMR (125 MHz, $CDCl_3$, $CD_3OD$) δ: 21.3, 28.1 (3), 48.8, 49.9, 52.5, 56.9, 69.5, 79.8, 127.3 (2), 128.1 (2), 128.5 (2), 129.6 (2), 133.0, 134.0, 139.9, 143.4, 155.4; HRMS (ESI) calcd for $C_{23}H_{29}ClN_2O_5S$ [M+Na]⁺503.1383; found 503.1391.

Example 3 tert-butyl ((R)-((3R,4S)-4-hydroxy-1-tosylpyrrolidin-3-yl)(4-(trifluoromethyl)phenyl)methyl)carbamate (Ic)

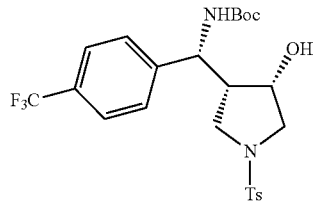 [SMILES: Cc1ccc(S(=O)(=O)N2C[C@H]([C@@H](NC(=O)OC(C)(C)C)c3ccc(C(F)(F)F)cc3)[C@H](O)C2)cc1]

Yield: 905 mg, 70%; colorless solid; mp 202-204° C.; $[\alpha]^D_{25}$+27.3 (c 0.3, $CHCl_3$); 95% ee (ChiracelOD-H (250× 4.6 mm), n-Hexane:i-PrOH, 80:20, 0.5 mL/min, 254 nm), $t_r$=93.6 min (minor), $t_r$=86.0 min (major); IR ($CHCl_3$, cm$^{-1}$): $\upsilon_{max}$ 1249, 1418, 1506, 1621, 1653, 1683, 2979, 3366; $^1$H NMR (500 MHz, $CDCl_3$) δ: 1.40 (s, 9H), 2.36-2.41 (m, 1H), 2.44 (s, 3H), 2.83 (t, J=9.7 Hz, 1H), 2.94 (t, J=7.9 Hz, 1H), 3.42 (d, J=11.6 Hz, 1H), 3.56 (d, J=10.3 Hz, 1H), 4.23 (s, 1H), 4.43 (br s, 1H), 4.64 (t, J=8.8 Hz, 1H), 4.93 (d, J=7.6 Hz, 1H), 7.29 (d, J=7.9 Hz, 2H), 7.35 (d, J=7.9 Hz, 2H), 7.64 (t, J=7.6 Hz, 4H); $^{13}$C NMR (125 MHz, $CDCl_3$) δ: 21.6, 28.2 (3), 48.0, 51.7, 52.8, 55.9, 70.0, 81.3, 122.6 (q, J=272.8 Hz) 126.4 (2), 127.2 (2), 127.5 (2), 129.6 (2), 130.1 (q, J=32.4 Hz), 134.2, 143.1, 143.3, 156.5; HRMS (ESI) calcd for $C_{24}H_{29}F_3N_2O_5S$ [M+Na]⁺ 537.1646; found 537.1648.

Example 4 tert-butyl ((R)-((3R,4S)-4-hydroxy-1-tosylpyrrolidin-3-yl)(p-tolyl)methyl)carbamate (Id)

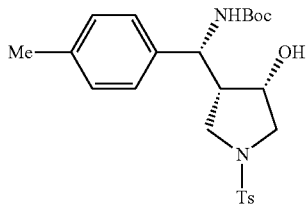 [SMILES: Cc1ccc([C@H](NC(=O)OC(C)(C)C)[C@H]2CN(S(=O)(=O)c3ccc(C)cc3)C[C@H]2O)cc1]

Yield: 810 mg, 70%; colorless solid; mp: 187-190° C. $[\alpha]^D_{25}$+25.1 (c 0.2, CHCl$_3$); 94% ee (ChiracelOD-H (250× 4.6 mm), n-Hexane:i-PrOH, 80:20, 0.5 mL/min, 254 nm), $t_r$=19.8 min (minor), $t_r$=14.3 min (major); IR (CHCl$_3$, cm$^{-1}$): $\upsilon_{max}$ 884, 1091, 1248, 1339, 1366, 1472, 1507, 1558, 1653, 1683, 2977, 3366; $^1$H NMR (400 MHz, CDCl$_3$) δ: 1.40 (s, 9H), 2.31-2.34 (m, 1H), 2.36 (s, 3H), 2.44 (s, 3H), 2.80 (dd, J=9.8, 11.5 Hz, 1H), 2.96 (dd, J=7.6, 9.3 Hz, 1H), 3.43 (d, J=11.5 Hz, 1H), 3.57 (dd, J=3.7, 12.9 Hz, 1H), 4.22 (s, 1H), 4.49 (dd, J=8.1, 11.0 Hz, 1H), 4.75 (br s, 1H), 4.83 (d, J=7.8 Hz, 1H), 7.09 (d, J=8.1 Hz, 2H), 7.18 (d, J=8.1 Hz, 2H), 7.29 (d, J=8.1 Hz, 2H), 7.65 (d, J=8.3 Hz, 2H); $^{13}$C NMR (100 MHz, CDCl$_3$): δ 21.1, 21.6, 28.2 (3), 48.3, 52.3, 52.9, 55.9, 69.9, 80.9, 126.6 (2), 127.4 (2), 129.5 (2), 130.0 (2), 134.1, 136.1, 138.5, 143.3, 156.7; HRMS (ESI) calcd for C$_{24}$H$_{32}$N$_2$O$_5$S [M+Na]$^+$ 483.1930; found 483.1926.

Example 5

(4R,4aR,7aS)-4-(naphthalen-2-yl)-6-tosylhexahydropyrrolo[3,4-e][1,3]oxazin-2(3H)-one (Ie)

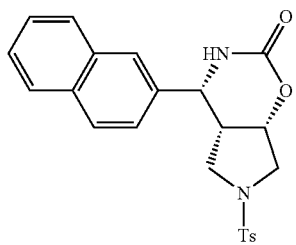 [SMILES: Cc1ccc(S(=O)(=O)N2C[C@H]3[C@@H](C2)OC(=O)N[C@H]3c2ccc3ccccc3c2)cc1]

Yield: 667 mg, 63%; colorless solid; mp 153-156° C.; $[\alpha]^D_{25}$+14.7 (c 0.3, CHCl$_3$); 99% ee (ChiracelOJ-H (250× 4.6 mm), n-Hexane:i-PrOH, 90:10, 0.5 mL/min, 254 nm), $t_r$=100.7 min (minor), $t_r$=80.1 min (major); IR (CHCl$_3$, cm$^{-1}$): $\upsilon_{max}$ 740, 1154, 1268, 1718, 2286, 2390, 3010, 3053, 3290; $^1$H NMR (400 MHz, CDCl$_3$) δ: 2.45 (s, 3H), 2.58-2.64 (m, 1H), 3.34-3.36 (m, 1H), 3.53-3.56 (m, 1H), 3.60-3.63 (m, 1H), 3.70-3.75 (m, 1H), 4.58-4.60 (m, 1H), 4.72-4.74 (m, 1H), 5.78 (s, 1H), 7.27-7.36 (m, 3H), 7.52-7.54 (m, 2H), 7.66 (s, 1H), 7.71-7.74 (m, 2H), 7.80-7.89 (m, 3H); $^{13}$C NMR (100 MHz, CDCl$_3$): δ 21.5, 42.2, 48.4, 53.9, 54.1, 75.8, 123.1, 124.9, 126.7, 127.0, 127.4 (2), 127.7, 127.9, 129.5, 129.9 (2), 133.1, 133.4, 137.4, 144.1, 151.9; HRMS (ESI) calcd for C$_{23}$H$_{22}$N$_2$O$_4$S [M+H]$^+$ 423.1378; found 423.1379.

Example 6

(4R, 4aR, 7aS)-4-(4-Bromophenyl)-6-tosylhexahydropyrrolo [3,4-e][1,3]oxazin-2(3H)-one (If)

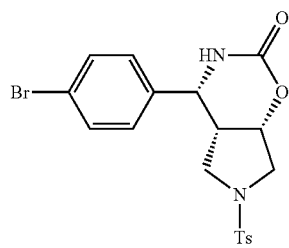 [SMILES: Cc1ccc(S(=O)(=O)N2C[C@H]3[C@@H](C2)OC(=O)N[C@H]3c2ccc(Br)cc2)cc1]

Yield: 690 mg, 61%; colorless solid; mp: 210-213° C.; $[\alpha]^D_{25}$+12.3 (c 0.3, CHCl$_3$); 98% ee (ChiracelOD-H (250× 4.6 mm), n-Hexane:i-PrOH, 80:20, 0.5 mL/min, 254 nm), $t_r$=34.5 min (minor), $t_r$=40.9 min (major); IR (CHCl$_3$, cm$^{-1}$): $\upsilon_{max}$ 742, 1160, 1271, 1705, 2286, 2350, 2999, 3290; $^1$H NMR (200 MHz, CDCl$_3$, CD$_3$OD) δ: 2.40 (s, 3H), 2.43-2.52 (m, 1H), 3.30 (t, J=9.7 Hz, 1H), 3.46-3.67 (m, 3H), 3.46-3.67 (m, 1H), 4.39 (d, J=2.7 Hz, 1H), 4.62-4.65 (m, 1H), 7.05 (d, J=8.6 Hz, 2H), 7.35 (d, J=7.5 Hz, 2H), 7.45 (d, J=7.5 Hz, 2H), 7.64 (d, J=8.4 Hz, 2H); $^{13}$C NMR (100 MHz, CDCl$_3$, CD$_3$OD) δ: 21.1, 41.7, 42.1, 52.3, 54.0, 75.5, 122.1, 127.1 (2), 127.2 (2), 129.7 (2), 132.0 (2), 132.8, 139.5, 144.1, 152.4; HRMS (ESI) calcd for C$_{19}$H$_{19}$BrN$_2$O$_4$S [M+Na]$^+$ 473.0141; found 473.0133.

Example 7

4R, 4aR, 7aS)-4-(4-Fluorophenyl)-6-tosylhexahydropyrrolo [3, 4-e][1,3]oxazin-2(3H)-one (Ig)

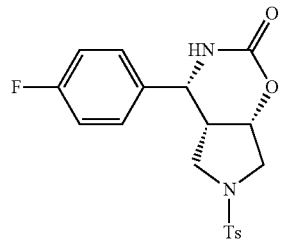 [SMILES: Cc1ccc(S(=O)(=O)N2C[C@H]3[C@@H](C2)OC(=O)N[C@H]3c2ccc(F)cc2)cc1]

Yield: 646 mg, 66%; colorless solid; mp: 207-211° C.; $[\alpha]^D_{25}$+12.3 (c 1.0, CHCl$_3$); 94% ee (ChiracelOD-H (250× 4.6 mm), n-Hexane:i-PrOH, 80:20, 0.5 mL/min, 254 nm), $t_r$=29.1 min (minor), $t_r$=24.0 min (major); IR (CHCl$_3$, cm$^{-1}$): $\upsilon_{max}$ 740, 1158, 1267, 1713, 2293, 2356, 3059, 3282; $^1$H NMR (400 MHz, CDCl$_3$) δ: 2.45 (s, 3H), 2.47-2.52 (m, 1H), 3.26 (t, J=8.7 Hz, 1H), 3.55-3.61 (m, 2H), 3.64 (dd, J=7.8, 9.6 Hz, 1H), 4.43 (t, J=3.7 Hz, 1H), 4.68-4.71 (m, 1H), 5.82 (br s, 1H), 7.08 (t, J=8.7 Hz, 2H), 7.20 (dd, J=8.7, 3.6 Hz, 2H), 7.36 (d, J=8.2 Hz, 2H), 7.69 (d, J=8.2 Hz, 2H); $^{13}$C NMR (100 MHz, CDCl$_3$): δ 21.6, 42.6, 48.4, 53.3, 54.0, 75.8, 116.3, 116.5, 127.5, 127.6, 127.7, 129.9 (2), 133.5, 136.0, 144.1, 151.7, 161.5 (d, J=250 Hz); HRMS (ESI) calcd for C$_{19}$H$_{19}$FN$_2$O$_4$S [M+Na]$^+$413.0942; found 413.0929.

Example 8 tert-Butyl ((R)-furan-2-yl((3R, 4S)-4-hydroxy-1-tosylpyrrolidin-3-yl) methyl) carbamate (Ih)

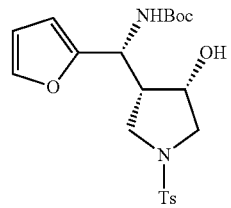 [SMILES: Cc1ccc(S(=O)(=O)N2C[C@H]([C@@H](NC(=O)OC(C)(C)C)c3ccco3)[C@H](O)C2)cc1]

Yield: 695 mg, 64%; colorless solid; mp: 136-139° C.; $[\alpha]^D_{25}$ −16.3 (c 0.5, CHCl$_3$); 90% ee (ChiracelOD-H (250× 4.6 mm), n-Hexane:i-PrOH, 80:20, 0.5 mL/min, 254 nm), t$_r$=19.8 min (minor), t$_r$=14.3 min (major); IR (CHCl$_3$, cm$^{-1}$): υ$_{max}$ 887, 1341, 1366, 1467, 1514, 1558, 1654, 1682, 3365; $^1$H NMR (400 MHz, CDCl$_3$) δ: 1.43 (s, 9H), 2.27-2.31 (m, 1H), 2.44 (s, 4H), 3.00 (t, J=8.0 Hz, 1H), 3.13 (t, J=10.0 Hz, 1H), 3.39 (t, J=8.0 Hz, 1H), 3.60 (t, J=8.0 Hz, 1H), 3.93 (d, J=6.8 Hz, 1H), 4.93-5.02 (m, 2H), 6.16 (d, J=3.3 Hz, 1H), 6.31 (dd, J=1.7, 3.0 Hz, 1H), 7.30-7.34 (m, 3H), 7.69 (d, J=8.1 Hz, 2H); $^{13}$C NMR (100 MHz, CDCl$_3$) δ: 21.6, 28.2 (3), 47.0 (2), 50.5, 52.2, 70.9, 80.8, 106.7, 110.5, 126.5, 127.6 (2), 129.8 (2), 142.3, 143.6, 152.0, 156.3; HRMS (ESI) calcd for C$_{21}$H$_{28}$N$_2$O$_6$S [M+Na]$^+$ 459.1560; found 459.1551.

Example 9 tert-Butyl ((R)-((3R, 4S)-4-hydroxy-1-tosylpyrrolidin-3-yl)(4-(methylthio) phenyl)methyl)carbamate (Ii)

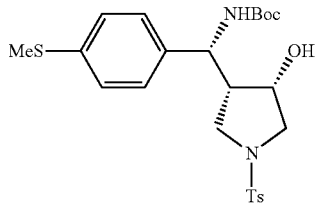

Yield: 801 mg, 65%; colorless solid; mp: 209-211° C.; $[\alpha]^D_{25}$+1.6 (c 0.1, CHCl$_3$); 88% ee (ChiracelOJ-H (250×4.6 mm), n-Hexane:i-PrOH, 80:20, 0.5 mL/min, 254 nm), t$_r$=34.0 min (minor), t$_r$=30.4 min (major); IR (CHCl$_3$, cm$^{-1}$): υ$_{max}$ 886, 1096, 1339, 1371, 1467, 1512, 1559, 1658, 1684, 2969, 3366; $^1$H NMR (500 MHz, CDCl$_3$) δ: 1.41 (s, 9H), 2.19-2.40 (m, 1H), 2.45 (s, 3H), 2.51 (s, 3H), 2.77 (dd, J=9.6, 11.8 Hz, 1H), 2.96 (dd, J=7.5, 9.1 Hz, 1H), 3.43 (d, J=11.4 Hz, 1H), 3.55-3.64 (m, 1H), 4.20-4.26 (m, 1H), 4.50 (dd, J=7.9, 10.7 Hz, 1H), 4.61 (br s, 1H), 4.77 (d, J=7.8 Hz, 1H), 7.13 (d, J=8.5 Hz, 2H), 7.21 (d, J=8.7 Hz, 2H), 7.30 (d, J=7.9 Hz, 2H), 7.66 (d, J=8.3 Hz, 2H); $^{13}$C NMR (125 MHz, CDCl$_3$) δ: 15.7, 21.6, 28.3 (3), 48.3, 52.2, 52.8, 56.0, 70.0, 81.1, 127.2 (2), 127.3 (2), 127.6 (2), 129.5 (2), 134.4, 135.8, 139.5, 143.1, 156.6; HRMS (ESI) calcd for C$_{24}$H$_{32}$N$_2$O$_5$S$_2$ [M+Na]$^+$ 515.1650; found 515.1645.

Example 10 tert-Butyl ((R)-((3R, 4S)-4-hydroxy-1-tosylpyrrolidin-3-yl)(thiophen-2-yl)methyl) carbamate (Ij)

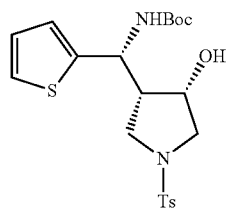 [SMILES: Cc1ccc(S(=O)(=O)N2C[C@H]([C@@H](NC(=O)OC(C)(C)C)c3cccs3)[C@H](O)C2)cc1]

Yield: 710 mg, 63%; colorless solid; mp: 186-189° C.; $[\alpha]^D_{25}$+37.3 (c 0.3, CHCl$_3$); 86% ee (ChiracelOJ-H (250× 4.6 mm), n-Hexane:i-PrOH, 80:20, 0.5 mL/min, 254 nm), t$_r$=18.0 min (minor), t$_r$=20.9 min (major); IR (CHCl$_3$, cm$^{-1}$): υ$_{max}$ 1345, 1370, 1472, 1521, 1565, 1655, 1685, 3369; $^1$H NMR (200 MHz, CDCl$_3$) δ: 1.42 (s, 9H), 2.38 (br s, 1H), 2.45 (s, 3H), 2.96-3.65 (m, 5H), 3.95-4.06 (m, 1H), 4.89-5.06 (m, 2H), 6.86-6.97 (m, 2H), 7.20 (t, J=4.8 Hz, 1H), 7.30 (d, J=7.9 Hz, 2H), 7.69 (dd, J=1.7, 8.2 Hz, 2H); $^{13}$C NMR (100 MHz, CDCl$_3$) δ: 21.5, 28.1 (3), 46.4, 48.3, 53.0, 55.8, 69.8, 80.9, 124.6, 125.2, 127.0, 127.4 (2), 129.4 (2), 134.1, 142.0, 143.0, 156.2; HRMS (ESI) calcd for C$_{21}$H$_{28}$N$_2$O$_5$S$_2$ [M+Na]$^+$ 475.1332; found 475.1320.

Example 11 tert-Butyl((R)-((3R, 4S)-4-hydroxy-1-tosylpyrrolidin-3-yl)(4-methoxyphenyl) methyl) carbamate (Ik)

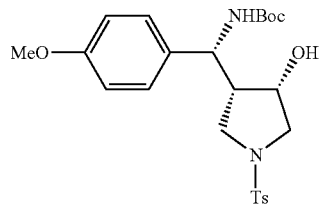

Yield: 883 mg, 74%; colorless solid; mp: 199-202° C.; $[\alpha]^D_{25}$+33.4 (c 0.3, CHCl$_3$); 100% ee (ChiracelOJ-H (250× 4.6 mm), n-Hexane:i-PrOH, 90:10, 0.5 mL/min, 254 nm), t$_r$=70.7 min; IR (CHCl$_3$, cm$^{-1}$): υ$_{max}$ 887, 1094, 1341, 1369, 1469, 1510, 1561, 1656, 1679, 2974, 3365; $^1$H NMR (500 MHz, CDCl$_3$): δ 1.41 (s, 9H), 2.29-2.40 (m, 1H), 2.45 (s, 3H), 2.78 (dd, J=9.2, 11.6 Hz, 1H), 2.95 (dd, J=7.8, 9.2 Hz, 1H), 3.44 (d, J=11.5 Hz, 1H), 3.59 (dd, J=3.7, 12.9 Hz, 1H), 3.83 (s, 3H), 4.18-4.25 (m, 1H), 4.47 (dd, J=7.8, 10.7 Hz, 1H), 4.73-4.75 (m, 2H), 6.88 (d, J=8.7 Hz, 2H), 7.13 (d, J=8.7 Hz, 2H), 7.30 (d, J=8.3 Hz, 2H), 7.66 (d, J=8.2 Hz, 2H); $^{13}$C NMR (125 MHz, CDCl$_3$): δ 21.6, 28.2 (3), 48.3, 52.4, 52.5, 55.3, 55.9, 70.0, 81.0, 114.8, 127.5 (2), 127.9 (2), 129.5 (2), 131.3 (2), 134.4, 143.1, 156.6, 159.7; HRMS (ESI) calcd for C$_{24}$H$_{32}$N$_2$O$_6$S[M+Na]$^+$499.1873; found 499.1861.

Example 12 ethyl (2S,3R,4R)-4-((R)-((tert-butoxycarbonyl)amino)(phenyl)methyl)-3-(2-ethoxy-2-oxoethyl)-1-tosylpyrrolidine-2-carboxylate (IA)

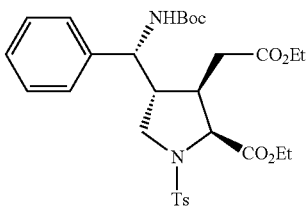

Yield: 1.17 g, 80%; colourless solid; mp: 150-151° C.; $[\alpha]^D_{25}$+34.3 (c 0.5, CHCl$_3$); 96% ee (ChiracelAS-H (250× 4.6 mm), n-Hexane:i-PrOH, 80:20, 0.5 mL/min, 254 nm), $t_r$=10.2 min (minor), $t_r$=11.1 min (major); IR (CHCl$_3$, cm$^{-1}$): $\upsilon_{max}$ 1162, 1214, 1345, 1499, 1736; $^1$H NMR (400 MHz, CDCl$_3$) δ: 1.22-1.26 (m, 6H), 1.41 (s, 9H), 1.89 (dd, J=5.7 and 11.8 Hz, 1H), 2.44 (s, 3H), 2.51-2.63 (m, 3H), 3.17 (t, J=9.0 Hz, 1H), 3.43 (t, J=8.5 Hz, 1H), 4.0-4.13 (m, 4H), 4.61 (d, J=7.7 Hz, 1H), 4.80 (brs, 1H), 4.99 (d, J=8.0 Hz, 1H), 7.14 (d, J=7.2 Hz, 2H), 7.26-7.33 (m, 5H), 7.68 (d, J=8.0 Hz, 2H); $^{13}$C NMR (100 MHz, CDCl$_3$): δ 14.0, 14.2, 21.6, 28.2, 29.7, 33.2, 40.5, 46.9, 48.3, 53.0, 60.6, 61.2, 63.2, 80.0, 125.9, 127.4, 128.9, 129.6, 135.6, 140.2, 143.4, 155.3, 170.4, 170.6; HRMS (ESI): C$_{30}$H$_{40}$N$_2$O$_8$S [M+Na]$^+$ 611.2402; found 611.2395.

Example 13 ethyl (2S,3R,4R)-4-((R)-((tert-butoxycarbonyl)amino)(4-chlorophenyl)methyl)-3-(2-ethoxy-2-oxo-ethyl)-1-tosylpyrrolidine-2-carboxylate (IB)

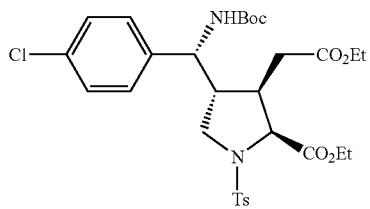

Yield: 1.04 g, 67%; colourless solid; mp: 155-156° C.; $[\alpha]^D_{25}$+23.4 (c 0.6, CHCl$_3$); 94% ee (ChiracelAS-H (250× 4.6 mm), n-Hexane:i-PrOH, 90:10, 0.5 mL/min, 254 nm), $t_r$=27.2 min (minor), $t_r$=30.6 min (major); IR (CHCl$_3$, cm$^{-1}$): $\upsilon_{max}$ 1156, 1238, 1512, 1711; $^1$H NMR (500 MHz, CDCl$_3$): δ 1.21 (t, J=7.0 Hz, 3H), 1.25 (t, J=7.3 Hz, 3H), 1.41 (s, 9H), 1.95 (dd, J=5.4, 11.6 Hz, 1H), 2.43 (s, 3H), 2.56-2.63 (m, 3H), 3.14 (t, J=7.9 Hz, 1H), 3.40 (s, 1H), 3.98-4.26 (m, 4H), 4.65 (d, J=7.3 Hz, 1H), 4.79 (s, 1H), 4.98 (d, J=9.4 Hz, 1H), 7.10 (d, J=8.5 Hz, 2H), 7.30 (t, J=8.2 Hz, 4H), 7.68 (d, J=7.2 Hz, 2H); $^{13}$C NMR (125 MHz, CDCl$_3$): δ 13.9, 14.1, 21.5, 28.1, 33.2, 40.4, 46.7, 48.0, 52.3, 60.7, 61.3, 63.1, 80.3, 127.3, 129.0, 129.6, 133.5, 135.3, 138.8, 143.7, 155.3, 170.3, 170.6; HRMS (ESI): calcd for C$_{30}$H$_{39}$ClN$_2$O$_8$S [M+Na]$^+$ 645.2013; found 645.2001.

Example 14 ethyl(2S,3R,4R)-4-((R)-((tert-butoxycarbonyl)amino)(4-(trifluoromethyl)phenyl)methyl)-3-(2-ethoxy-2-oxoethyl)-1-tosylpyrrolidine-2-carboxylate (IC)

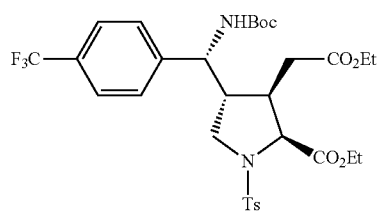

Yield: 1.11 g, 68%; Colourless solid; mp: 169-170° C.; $[\alpha]^D_{25}$+12.1 (c 0.4, CHCl$_3$); 99% ee (ChiracelOJ-H (250× 4.6 mm), n-Hexane:i-PrOH, 90:10, 0.5 mL/min, 254 nm), $t_r$=18.9 min (minor), $t_r$=27.9 min (major); IR (CHCl$_3$, cm$^{-1}$): $\upsilon_{max}$ 1159, 1319, 1513, 1599, 1735; $^1$H NMR (500 MHz, CDCl$_3$) δ: 1.23 (dd, J=7.3, 9.1 Hz, 6H), 1.40 (s, 9H), 1.99 (dd, J=5.4, 10.6 Hz, 1H), 2.43 (s, 3H), 2.54-2.60 (m, 2H), 2.67 (s, 1H), 3.20 (t, J=8.5 Hz, 1H), 3.37 (t, J=7.6 Hz, 1H), 4.0-4.14 (m, 4H), 4.64 (d, J=7.3 Hz, 1H), 4.88 (s, 1H), 5.26 (d, J=8.8 Hz, 1H), 7.31 (t, J=8.2 Hz, 4H), 7.57 (d, J=7.9 Hz, 2H), 7.68 (d, J=8.2 Hz, 2H); $^{13}$CNMR (125 MHz, CDCl$_3$) δ: 13.9, 14.1, 21.6, 28.2, 33.2, 40.5, 46.7, 47.9, 52.7, 60.7, 61.3, 63.0, 80.3, 122.8 (q, J=271.8 Hz), 125.9, 126.4, 127.1 (q, J=28.3 Hz), 127.4, 129.6, 130.1 (q, J=33.3 Hz), 135.5, 143.6 (d, J=271.8 Hz), 155.3, 170.3, 170.5; HRMS (ESI): calcd for C$_{31}$H$_{39}$F$_3$N$_2$O$_8$S [M+Na]$^+$ 679.2271; found 679.2271.

Example 15 ethyl (2S,3R,4R)-4-((R)-((tert-butoxycarbonyl)amino)(p-tolyl)methyl)-3-(2-ethoxy-2-oxoethyl)-1-tosylpyrrolidine-2-carboxylate (ID)

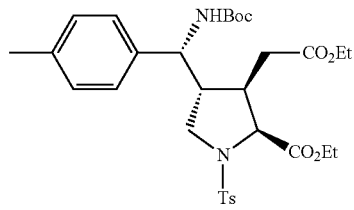

Yield: 1.17 g, 78%; colourless solid; mp: 177-178° C.; $[\alpha]^D_{25}$+10.9 (c 0.7, CHCl$_3$); 93% ee (ChiracelAS-H (250× 4.6 mm), n-Hexane:i-PrOH, 90:10, 0.5 mL/min, 254 nm), $t_r$=27.2 min (minor), $t_r$=39.4 min (major); IR (CHCl$_3$, cm$^{-1}$): $\upsilon_{max}$ 1162, 1214, 1344, 1499, 1734; $^1$H NMR (500 MHz, CDCl$_3$) δ: 1.22 (quint, J=7.0 Hz, 6H), 1.39 (s, 9H), 1.88 (dd, J=4.5, 11.6 Hz, 1H), 2.31 (s, 3H), 2.43 (s, 3H), 2.49-2.62 (m, 3H), 3.17 (t, J=8.8 Hz, 1H), 3.46 (t, J=7.6 Hz, 1H), 3.98-4.13 (m, 4H), 4.60 (d, J=7.6 Hz, 1H), 4.74 (s, 1H), 5.02 (d, J=8.5 Hz, 1H), 7.02 (d, J=7.9 Hz, 2H), 7.09 (d, J=7.9 Hz, 2H), 7.29 (d, J=7.9 Hz, 2H), 7.68 (d, J=8.2 Hz, 2H); $^{13}$C NMR (125 MHz, CDCl$_3$): δ 13.9, 14.1, 21.0, 21.5, 28.2, 33.2, 40.5, 46.9, 48.4, 52.8, 60.5, 61.1, 63.2, 79.8, 125.8, 127.3, 129.6, 135.5, 137.2, 143.3, 155.3, 170.4, 170.6; HRMS (ESI+, m/z): calcd for $C_{31}H_{42}N_2O_8S$ [M+Na]$^+$ 625.2554; found 625.2558.

Example 16 ethyl (2S,3R,4R)-4-((R)-((tert-butoxycarbonyl)amino)(naphthalen-2-yl)methyl)-3-(2-ethoxy-2-oxoethyl)-1-tosylpyrrolidine-2-carboxylate (IE)

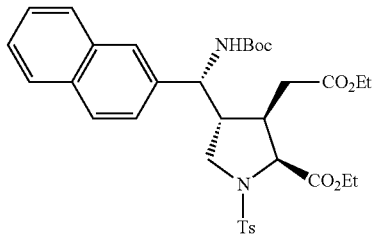

Yield: 1.26 g, 79%; colourless solid; mp: 160-161° C.; $[\alpha]^D_{25}$+22.7 (c 0.5, CHCl$_3$); 92% ee (Chiracel AS-H (250× 4.6 mm), n-Hexane:i-PrOH, 80:20, 0.5 mL/min, 254 nm), t$_r$=17.8 min (minor), t$_r$=26.9 min (major); IR (CHCl$_3$, cm$^{-1}$): $\upsilon_{max}$ 1163, 1214, 1514, 1738; $^1$H NMR (400 MHz, CDCl$_3$) δ: 1.21 (t, J=7.0 Hz, 6H), 1.41 (s, 9H), 1.95 (dd, J=4.8, 11.9 Hz, 1H), 2.41 (s, 3H), 2.60 (d, J=11 Hz, 2H), 2.78 (s, 1H), 3.25 (t, J=8.8 Hz, 1H), 3.45 (t, J=7.5 Hz, 1H), 3.99-4.13 (m, 4H), 4.65 (d, J=7.5 Hz, 1H), 4.98 (s, 1H), 5.19 (s, 1H), 7.26 (d, J=8.0 Hz, 3H), 7.46 (t, J=3.9 Hz, 2H), 7.60 (s, 1H), 7.67 (d, J=7.8 Hz, 2H), 7.77 (d, J=8.3 Hz, 3H); $^{13}$C NMR (100 MHz, CDCl$_3$) δ: 13.9, 14.1, 21.5, 28.2, 33.3, 40.6, 46.8, 48.3, 53.2, 60.5, 61.2, 63.2, 80.0, 123.9, 124.6, 126.1, 126.4, 127.3, 127.6, 127.9, 128.9, 129.6, 132.7, 133.2, 135.5, 137.5, 143.4, 155.4, 170.4, 170.6; HRMS (ESI): calcd for $C_{34}H_{42}N_2O_8S$ [M+Na]$^+$ 661.2559; found 661.2555.

Example 17 ethyl (2S,3R,4R)-4-((R)-(4-bromophenyl)((tert-butoxycarbonyl)amino)methyl)-3-(2-ethoxy-2-oxoethyl)-1-tosylpyrrolidine-2-carboxylate (IF)

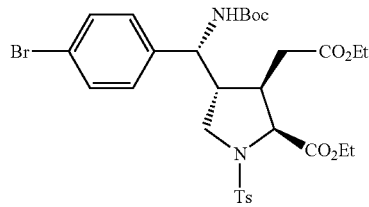

Yield: 1.27 g, 76%; Colourless solid; mp:161-163° C.; $[\alpha]^D_{25}$+17.4 (c 0.5, CHCl$_3$); 100% ee (ChiracelOJ-H (250× 4.6 mm), n-Hexane:i-PrOH, 80:20, 0.5 mL/min, 254 nm), t$_r$=24.0 min; IR (CHCl$_3$, cm$^{-1}$): $\upsilon_{max}$ 1155, 1237, 1737, 1511, 1718; $^1$H NMR (200 MHz, CDCl$_3$) δ: 1.21 (q, J=7.2, 7.33 Hz, 6H), 1.40 (s, 9H), 1.96 (dd, J=6.9, 10.48 Hz, 1H), 2.44 (s, 3H), 2.52-2.60 (m, 4H), 3.15 (t, J=8.9 Hz, 1H), 3.39 (t, J=8.4 Hz, 1H), 4.0-4.17 (m, 4H), 4.62 (d, J=7.0 Hz, 1H), 4.78 (s, 1H), 5.04 (d, J=9.4 Hz, 1H), 7.03 (d, J=8.4 Hz, 2H), 7.28 (t, J=8.0 Hz, 2H), 7.42 (d, J=8.4 Hz, 2H), 7.66 (d, J=8.2 Hz, 2H); $^{13}$C NMR (50 MHz, CDCl$_3$) δ: 13.9, 14.1, 21.5, 28.2, 33.2, 40.5, 46.7, 48.2, 52.7, 60.6, 61.2, 63.1, 80.1, 121.5, 127.3, 127.8, 129.6, 131.9, 135.5, 139.6, 143.4, 155.3, 156.3 170.3, 170.5; HRMS (ESI): calcd for $C_{30}H_{39}BrN_2O_8S$[M+Na]$^+$ 689.1507; found 689.1517.

Example 18 ethyl (2S,3R,4R)-4-((R)-((tert-butoxycarbonyl)amino)(4-fluorophenyl)methyl)-3-(2-ethoxy-2-oxoethyl)-1-tosylpyrrolidine-2-carboxylate (IG)

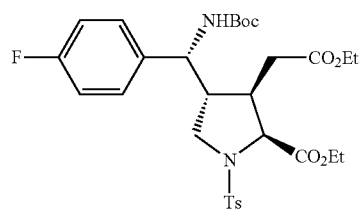

Yield: 1.07 g, 71%; colourless solid; mp: 148-150° C.; $[\alpha]^D_{25}$+13.2 (c 0.5, CHCl$_3$); 92% ee (Chiracel AS-H (250× 4.6 mm), n-Hexane:i-PrOH, 90:10, 0.5 mL/min, 254 nm), t$_r$=17.5 min (minor), t$_r$=22.7 min (major); IR (CHCl$_3$, cm$^{-1}$): $\upsilon_{max}$ 1161, 1214, 1344, 1510, 1736; $^1$H NMR (500 MHz, CDCl$_3$): δ 1.23 (dd, J=7.3, 7.0 Hz, 6H), 1.40 (s, 9H), 1.91 (dd, J=4.2, 12.2 Hz, 1H), 2.44 (s, 3H), 2.50-2.53 (m, 2H), 2.63 (s, 1H), 3.16 (t, J=7.93 Hz, 1H), 3.43 (bs, 1H), 4.0-4.17 (m, 4H), 4.62 (d, J=7.6 Hz, 1H), 4.77 (s, 1H), 5.06 (s, 1H), 7.00 (t, J=8.2 Hz, 2H), 7.14 (dd, J=5.1, 3.0 Hz, 2H), 7.30 (d, J=7.9 Hz, 2H), 7.68 (d, J=7.9 Hz, 2H); $^{13}$C NMR (125 MHz, CDCl$_3$): δ 13.9, 14.1, 21.6, 28.2, 28.3, 33.2, 40.6, 46.8, 48.3, 52.6, 60.6, 61.2, 63.2, 80.1, 115.7, 115.9, 127.3, 127.6, 127.7, 129.6, 135.5, 136.2, 143.5, 155.3, 161.0 (d, J=247 Hz), 170.4, 170.5; HRMS (ESI): calcd for $C_{30}H_{39}FN_2O_8S$ [M+Na]$^+$ 629.2303; found 629.2307.

Example 19 ethyl (2S,3R,4R)-4-((R)-((tert-butoxycarbonyl)amino)(furan-2-yl)methyl)-3-(2-ethoxy-2-oxoethyl)-1-tosylpyrrolidine-2-carboxylate (IH)

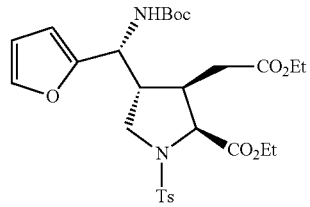 [SMILES: CCOC(=O)C[C@@H]1[C@@H]([C@@H](NC(=O)OC(C)(C)C)c2ccco2)CN(S(=O)(=O)c2ccc(C)cc2)[C@@H]1C(=O)OCC]

Yield: 0.861 g, 60%; gum; $[\alpha]^D_{25}$+34.0 (c 0.9, CHCl$_3$); 92% ee (Chiracel AS-H (250×4.6 mm), n-Hexane:i-PrOH, 80:20, 0.5 mL/min, 254 nm), t$_r$=17.0 min (minor), t$_r$=20.7 min (major); IR (CHCl$_3$, cm$^{-1}$): $\upsilon_{max}$ 1162, 1344, 1513, 1599, 1735; $^1$H NMR (500 MHz, CDCl$_3$) δ: 1.23 (t, J=7.3 Hz, 3H), 1.26 (t, J=7.0 Hz, 3H), 1.41 (s, 9H), 1.95 (dd, J=11.3, 11.6 Hz, 1H), 2.44 (s, 3H), 2.46-2.50 (m, 1H), 2.69-2.70 (m, 2H), 3.20 (t, J=7.4 Hz, 1H), 3.57 (t, J=8.8 Hz, 1H), 4.02-4.07 (m, 1H), 4.11 (q, J=7.0 Hz, 4H), 4.60 (d, J=8.2 Hz, 1H), 4.84 (s, 1H), 6.14 (d, J=3.0 Hz, 1H), 6.29 (s, 1H), 7.30 (s, 1H), 7.32 (s, 2H), 7.71 (d, J=8.2 Hz, 2H); $^{13}$C NMR (125 MHz, CDCl$_3$) δ: 14.0, 14.2, 21.6, 28.2, 33.0, 40.2, 45.5, 47.4, 48.4, 60.6, 61.2, 63.0, 80.2, 106.6, 110.5, 127.4, 129.6, 135.8, 142.2, 143.3, 152.6, 155.3, 170.4, 170.7; HRMS (ESI+, m/z): calcd for C$_{28}$H$_{38}$N$_2$O$_9$S)[M+Na]$^+$ 601.2195; found 601.2197.

Example 20

A. Preparation of Corey-Chaykovsky Reagent:

In a flask, under inert atmospheric condition, DMSO (10 mL) was added to NaH (2 mmol, washed with hexane) at rt. Trimethylsulfoxonium iodide (2 mmol) was added to the above solution and stirred for 30 min to generate sulfur ylide (Corey-Chaykovsky reagent).

B. General Experimental Procedure for the Synthesis of Substituted Pyrazolidines (2a-2m):

To a cold solution of diisopropyl azodicarboxylate (DIAD) (1 mmol) and L-proline (10 mol %) in CH$_3$CN (10 mL) at 0° C. was added 3-phenylpropionaldehyde 1Va' (1.2 mmol) and the mixture was stirred for 3 h at 0° C. This was followed by addition of ethyl 2-(triphenyl-15-phosphanylidene) acetate (2 mmol) and stirred further for 2 h.

After stirring the above reaction mixture for 2 h, Corey-Chaykovsky reagent (prepared as described below), was added into it at room temperature under nitrogen atmosphere and stirred for 2 h.

The reaction was then quenched with sat. NH$_4$Cl solution and then organic layer was extracted with ethyl acetate (10 mL×3 times) washed with brine, dried over Na$_2$SO$_4$, concentrated, product purified by silica gel column chromatography (230-400 mesh) using petroleum ether and EtOAc (80:20) as eluent to afford a pure product 2a to 2m depending on choice of substrate (1a to 1h). The enantiomeric ratios of all products were determined by chiral-phase HPLC analysis.

Example 21

Diisopropyl (3R,4S)-3-benzyl-4-(2-ethoxy-2-oxoethyl)pyrazolidine-1,2-dicarboxylate (2a)

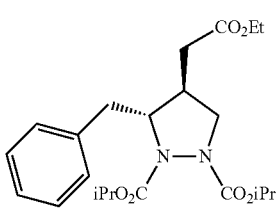

$^1$H NMR (200 MHz, CDCl3): δ 1.12-1.31 (m, 15H); 2.18 (d, 2H, J=8 Hz); 2.54-2.60 (dd, 1H, J=4, 8 Hz); 2.61-2.70 (dd, 1H, J=6, 12 Hz); 2.90-3.00 (m, 2H); 4.03-4.28 (m, 4H); 4.82-5.05 (m, 2H); 7.24-7.28 (m, 5H) ppm; $^{13}$C NMR (50 MHz, CDCl3): δ 14.04, 21.67, 21.79, 21.91, 37.20, 40.26, 41.32, 51.70, 60.46, 65.45, 69.68, 69.82, 126.44, 128.23, 129.24, 137.39, 156.08, 156.28, 170.79 ppm. ESI-MS: m/z 421.2 [M+1]

Example 22

Diethyl (3R, 4S)-3-benzyl-4-(2-ethoxy-2-oxoethyl)pyrazolidine-1,2-dicarboxylate (2b)

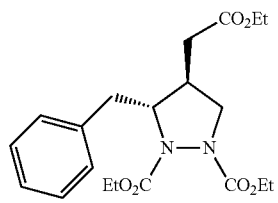 [SMILES: CCOC(=O)C[C@H]1CN(C(=O)OCC)N(C(=O)OCC)[C@@H]1Cc1ccccc1]

$^1$H NMR (200 MHz, CDCl3): δ 1.16-1.35 (m, 9H); 2.165 (d, 2H, J=6 Hz); 2.54-2.61 (m, 1H); 2.63-2.73 (dd, 1H, J=6, 12 Hz); 2.90-3.03 (m, 2H); 4.02-4.29 (m, 8H), 7.24-7.27 (m, 5H) ppm; $^{13}$C NMR (50 MHz, CDCl3): δ 14.13, 14.35, 37.12, 40.33, 41.35, 51.98, 60.60, 62.22, 65.61, 77.32, 126.60, 128.36, 129.35, 137.29, 156.64, 156.78, 170.87 ppm. ESI-MS: m/z 393.2 [M+1].

Example 23

Di-tert-butyl (3R,4S)-3-benzyl-4-(2-ethoxy-2-oxoethyl)pyrazolidine-1,2-dicarboxylate (2c)

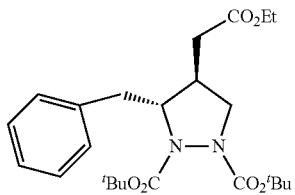 [SMILES: CCOC(=O)C[C@H]1CN(C(=O)OC(C)(C)C)N(C(=O)OC(C)(C)C)[C@@H]1Cc1ccccc1]

$^1$H NMR (200 MHz, CDCl3): δ 1.23 (t, 3H); 1.37-1.50 (m, 18H); 2.20 (d, 2H, J=8 Hz); 2.53-2.71 (m, 2H); 2.83-2.99 (m, 2H); 3.99-4.22 (m, 4H); 7.19-7.26 (m, 5H) ppm; $^{13}$C NMR (50 MHz, CDCl3): δ 14.11, 27.97, 28.14, 37.39, 40.19, 41.32, 51.40, 60.51, 65.35, 80.86, 126.39, 128.21, 129.37, 137.67, 155.26, 155.63, 171.00 ppm.

Example 24 diisopropyl (3R,4S)-4-(2-ethoxy-2-oxoethyl)-3-(naphthalen-2-ylmethyl)pyrazolidine-1,2-dicarboxylate (2d)

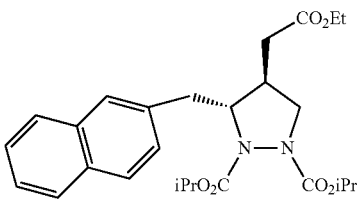

$^1$H NMR (200 MHz, CDCl3): δ 1.09-1.17 (t, 3H, J=8 Hz); 1.22-1.35 (m, 12H); 2.62-2.68 (m, 1H); 2.88-3.06 (m, 2H); 3.61 (bs, 1H); 3.91-4.01 (quart. 2H, J=6 Hz); 4.24-4.39 (m, 2H); 4.85-5.10 (dsept. 2H, J=6 Hz); 7.36-8.24 (m, 8H) ppm; $^{13}$C NMR (50 MHz, CDCl3): δ 13.85, 21.49, 21.61, 21.85, 36.72, 38.34, 41.83, 52.05, 60.27, 63.82, 69.50, 69.91, 123.55, 125.39, 125.94, 127.39, 127.50, 128.59, 131.79, 133.29, 133.67, 155.61, 156.49, 170.60 ppm. ESI-MS: m/z 471.3 [M+1]

Example 25

Diisopropyl (3R,4S)-4-(2-ethoxy-2-oxoethyl)-3-(4-methoxybenzyl)pyrazolidine-1,2-dicarboxylate (2e)

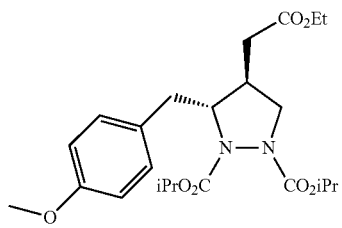

$^1$H NMR (200 MHz, CDCl3): δ 1.20-1.31 (m, 15H); 2.16-2.20 (d, 2H, J=8 Hz); 2.54-2.64 (m, 2H); 2.84-2.99 (m, 2H); 3.78 (s, 3H); 4.01-4.17 (m, 4H); 4.86-5.01 (m, 2H); 6.78-6.82 (d, 2H, J=8 Hz); 7.15-7.19 (d, 2H, J=8 Hz) ppm; $^{13}$C NMR (50 MHz, CDCl3): δ 14.20, 21.88, 37.35, 39.45, 41.31, 51.86, 55.07, 60.64, 65.73, 69.67, 69.85, 69.97, 113.80, 114.06, 129.55, 130.32, 156.43, 158.37, 171.03 ppm. ESI-MS: m/z 451.2 [M+1]

Example 26

Diisopropyl(3R,4S)-3-(3-(benzyloxy)propyl)-4-(2-ethoxy-2-oxoethyl)pyrazolidine-1,2-dicarboxylate (2f)

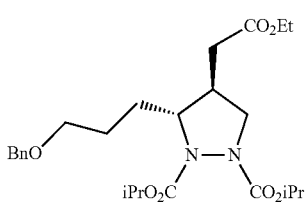

$^1$H NMR (200 MHz, CDCl3): δ 1.20-1.29 (m 15H); 1.62-1.77 (m, 4H); 2.27-2.52 (m, 3H); 2.90-2.98 (dd, 1H, J=6 Hz); 3.93-3.99 (m, 1H); 4.07-4.48 (m, 3H); 4.48 (s, 2H); 4.87-5.02 (septet, 2H, J=6 Hz); 7.30 (s, 5H) ppm; $^{13}$C NMR (50 MHz, CDCl3): δ 14.01, 21.80, 26.27, 30.34, 37.54, 41.48, 51.36, 60.46, 63.90, 69.55, 69.65, 72.61, 77.20, 127.25, 128.08, 138.37, 156.45, 156.65, 170.91 ppm. ESI-MS: m/z 479.3 [M+1]

Example 27

Diisopropyl (3R,4S)-4-(2-ethoxy-2-oxoethyl)-3-(4-(methylthio)benzyl)pyrazolidine-1,2-dicarboxylate (2g)

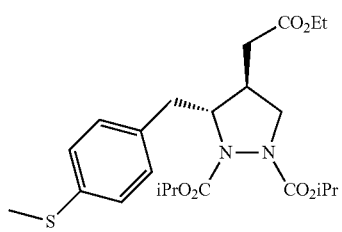

$^1$H NMR (200 MHz, CDCl3): δ 1.12-1.31 (m, 15H); 2.20-2.23 (d, 2H); 2.46 (s, 3H); 2.55-2.69 (m, 2H); 2.81-3.00 (m, 2H); 4.04-4.15 (quart. 2H, J=8 Hz); 4.17-4.27 (m, 2H); 4.85-5.07 (m, 2H); 7.18 (s, 4H) ppm; $^{13}$C NMR (50 MHz, CDCl3): δ 14.16, 15.99, 21.77, 37.33, 39.73, 41.38, 51.76, 60.65, 65.53, 69.98, 126.82, 129.85, 134.47, 136.37, 156.31, 170.95 ppm. ESI-MS: m/z 467.2 [M+1]

Example 28

Diisopropyl (3R,4S)-4-(2-ethoxy-2-oxoethyl)-3-(4-methylbenzyl)pyrazolidine-1,2-dicarboxylate (2h)

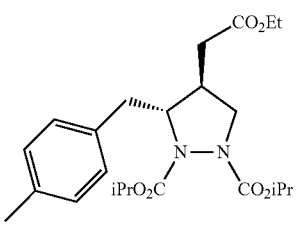

$^1$H NMR (200 MHz, CDCl3): δ 1.15-1.30 (m, 15H); 2.15-2.17 (d, 2H); 2.31 (s, 3H); 2.57-2.66 (m, 2H); 2.92-2.96 (m, 2H); 4.05-4.11 (m, 3H); 4.21-4.24 (dd, 1H, J=4 Hz); 4.88-4.95 (quint. 1H, J=4 Hz); 4.97-5.01 (quint. 1H, J=4 Hz); 7.06-7.08 (d, 2H, J=8 Hz); 7.12-7.14 (d, 2H, J=8 Hz) ppm; $^{13}$C NMR (50 MHz, CDCl3): δ 14.18, 21.08, 21.84, 22.06, 37.39, 39.94, 41.33, 51.88, 60.60, 65.60, 69.83, 69.96, 129.09, 129.24, 134.34, 135.91, 156.29, 156.46, 170.96 ppm. ESI-MS: m/z 435.2 [M+1]

Example 29

Diisopropyl(3R,4S)-4-(2-ethoxy-2-oxoethyl)-3-((6-nitrobenzo[d][1,3]dioxol-5-yl)methyl)pyrazolidine-1,2-dicarboxylate (2i)

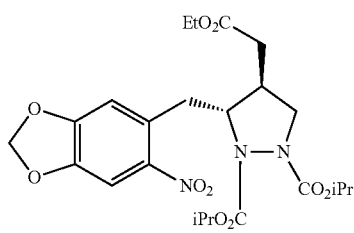

$^1$H NMR (200 MHz, CDCl3): δ 1.07-1.38 (m, 15H); 2.39-2.76 (m, 5H); 2.90-2.99 (dd, 1H, J=2, 12 Hz); 3.42-3.50 (dd, 1H, J=2, 12 Hz); 4.17 (q, 3H, J=8 Hz); 4.73 (sep, 1H, J=6 Hz); 6.08 (s, 2H); 7.04 (s, 1H); 7.65 (s, 1H) ppm; $^{13}$C NMR (50 MHz, CDCl3): δ 14.14, 21.53, 21.67, 21.93, 22.04, 30.76, 36.65, 39.18, 43.05, 52.05, 60.78, 64.82, 69.70, 70.27, 102.71, 105.35, 112.57, 131.19, 142.68, 146.79, 151.53, 156.18, 170.93 ppm.

Example 30

Di-tert-butyl(3R,4S)-4-(2-ethoxy-2-oxoethyl)-3-((6-nitrobenzo[d][1,3]dioxol-5-yl)methyl)pyrazolidine-1,2-dicarboxylate (2j)

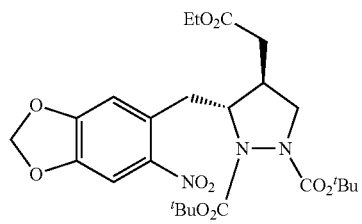 [SMILES: CCOC(=O)C[C@H]1CN(C(=O)OC(C)(C)C)N(C(=O)OC(C)(C)C)[C@@H]1Cc1cc2c(cc1[N+](=O)[O-])OCO2]

$^1$H NMR (200 MHz, CDCl3): δ 1.25-1.32 (m, 12H); 2.38-0.70 (m, 4H); 2.90-2.99 (m, 1H); 3.35-3.43 (dd, 1H, J=4, 8 Hz); 4.13-4.31 (m, 4H); 6.08 (s, 2H); 7.10 (s, 1H); 7.54 (s, 1H) ppm; $^{13}$C NMR (50 MHz, CDCl3): δ 14.28, 27.95, 28.38, 37.05, 39.06, 43.04, 60.87, 80.98, 81.55, 102.69, 105.48, 112.86, 131.41, 142.84, 146.74, 151.45, 155.52, 171.10 ppm.

Example 31

Diisopropyl(3R,4S)-3-((6-cyanobenzo[d][1,3]dioxol-5-yl)methyl)-4-(2-ethoxy-2-oxoethyl)pyrazolidine-1,2-dicarboxylate (2k)

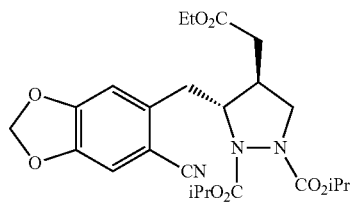

$^1$H NMR (200 MHz, CDCl3): δ 1.06-1.34 (m, 15H); 2.29-3.17 (m, 6H); 4.08-4.30 (m, 4H); 4.75-5.09 (m, 2H); 6.03 (s, 2H); 6.98 (s, 1H); 7.05 (s, 1H) ppm; $^{13}$C NMR (50 MHz, CDCl3): δ 14.16, 21.67, 21.80, 22.06, 36.91, 38.61, 42.13, 51.85, 60.85, 64.97, 69.99, 70.28, 102.12, 104.76, 110.93, 111.64, 117.93, 138.43, 146.58, 151.39, 156.06, 170.77 ppm. ESI-MS: m/z 490.2 [M+1]

Example 32

Diisopropyl (3R,4S)-4-(2-ethoxy-2-oxoethyl)-3-methylpyrazolidine-1,2-dicarboxylate (2l)

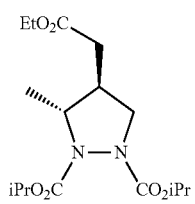

$^1$H NMR (200 MHz, CDCl3): δ 1.24-1.31 (m, 18H); 2.29-2.47 (m, 3H); 2.86-2.93 (m, 1H); 3.88-3.96 (m, 1H); 4.14 (q, 2H, J=8 Hz); 4.96 (sep, 2H, J=6 Hz) ppm; $^{13}$C NMR (50 MHz, CDCl3): δ 14.05, 19.64, 21.82, 21.90, 36.67, 43.25, 51.81, 59.94, 60.53, 69.52, 69.71, 77.20, 155.97, 156.82, 170.94 ppm.

Example 33

Diisopropyl (3R,4S)-4-(2-ethoxy-2-oxoethyl)-3-propylpyrazolidine-1,2-dicarboxylate (2m)

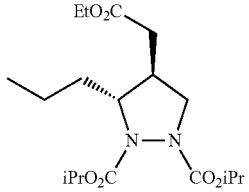

$^1$H NMR (200 MHz, CDCl3): δ 0.945 (t, 3H, J=6 Hz); 1.22-1.30 (m, 15H); 1.35-1.46 (m, 4H); 2.28-2.55 (m, 3H); 2.89-2.98 (dd, 1H, J=6, 12 Hz); 3.94 (bs, 1H); 4.09-4.22 (m, 3H); 4.90-5.02 (m, 2H) ppm; $^{13}$C NMR (50 MHz, CDCl3): δ 13.65, 14.18, 19.31, 21.95, 35.96, 37.82, 41.58, 51.52, 60.59, 63.98, 69.58, 77.35, 156.69, 171.12 ppm. ESI-MS: m/z 373.2 [M+1]

Anti-Mycobacterial Activity Assay:

Anti-mycobacterial activity of the synthesized compounds was performed with *Mycobacterium smegmatis* MC$^2$155 strain by performing a growth inhibition assay by agar dilution followed turbidometry method. The assay was semi-throughput and conducted in a 96 well plate (sterile). Isolated single colonies of *M. smegmatis* MC$^2$ 155 (ATCC 14468) grown on 7H10 agar plate were grown overnight in Middlebrook 7H9 medium (0.47% Middlebrook 7H9 broth base, 10% ADS, 0.2% glycerol, and 0.1% Tween-80) to mid exponential phase at 37° C. When the OD of this culture reached approximately 0.8, a secondary culture was inoculated in 5 ml Middlebrook 7H9 medium. The secondary culture was incubated overnight and allowed to grow at 37° C. to early log phase (OD$_{600}$≈0.3). For the anti-mycobacterial assay, 98 μl of 1:1000-folds dilution of secondary culture was dispensed into 96-well microtiter plate per well along with 2 μl of test compound in triplicate. 240 μl of sterile water were added to each well of the peripheral rows of 96-well plate to minimize media evaporation during assay incubation. The final concentration of the test compound in each well was 30 μM. Bacterial growth was assessed after 32 hours of incubation by measuring turbidity at 600 nm OD$_{600}$ values using TECAN Infinite 200 PRO™ (Tecan Instruments, Switzerland). Depending upon the percentage of growth, the percentage of inhibition was calculated at the standard concentration of 30 μM. Isoniazid and Rifampicin were included in every assay plate as positive controls of growth inhibition using stock solutions of INH (10 mg/mL, HiMedia) and Rifampicin (10 mg/mL, HiMedia) to achieve the final concentration of 16 μg/mL for INH and 2 μg/mL for Rifampicin. Additional controls, DMSO (solvent without compound) and medium without inoculums, were included in all the assay plates avoiding intra assay variability. The results were analyzed as the percentage of growth inhibition.

| Sample code | % Inhibition |
|---|---|
| IG | 18.227 |
| IF | 10.837 |
| IA | 13.547 |
| IE | 20.690 |
| IC | 0.493 |
| 2i | 29.310 |
| 2g | 24.877 |
| 2e | 14.039 |

We claim:

1. A novel substituted 5 membered heterocyclic compounds of Formula I and its enantiomers,

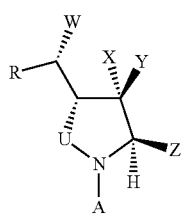

I wherein,
i) when, U is CH$_2$ then A is Ts; W is NHBoc; R is aryl, substituted aryl or heteroaryl (wherein substituents are seleceted from Br, Cl, F, CF$_3$, CH$_3$, —OCH$_3$, and —SCH$_3$); and
  a) X is OH, Y and Z are Hydrogen; or
  b) X is H, Y is —CH$_2$COOEt and Z is —COOEt;
ii) when, U is NCOOR' then A is COOR'; W is H; R is H, aryl, substituted aryl (wherein substituents are selected from —OCH$_3$, —SCH$_3$, CH$_3$, NO$_2$, and —OCH$_2$O—), alkyl, linear or branched alkyl substituted by —OBn; X is —CH$_2$COOEt; Y is H; Z is H and R' is alkyl-linear or branched.

2. The novel compounds of Formula I as claimed in claim 1, wherein compound of Formula I is selected from the group consisting of:
tert-butyl((R)-((3R,4S)-4-hydroxy-1-tosylpyrrolidin-3-yl)(phenyl)methyl)carbamate (Ia);
tert-butyl ((R)-(4-chlorophenyl)((3R,4S)-4-hydroxy-1-tosylpyrrolidin-3-yl)methyl)carbamate (Ib);
tert-butyl ((R)-((3R,4S)-4-hydroxy-1-tosylpyrrolidin-3-yl)(4-(trifluoromethyl)phenyl)methyl)carbamate(Ic);
tert-butyl ((R)-((3R,4S)-4-hydroxy-1-tosylpyrrolidin-3-yl)(p-tolyl)methyl)carbamate (Id);
(4R,4aR,7aS)-4-(naphthalen-2-yl)-6-tosylhexahydropyrrolo[3,4-e][1,3]oxazin-2(3H)-one (Ie);
(4R,4aR,7aS)-4-(4-Bromophenyl)-6-tosylhexahydropyrrolo[3,4-e][1,3]oxazin-2(3H)-one (If);
4R,4aR,7aS)-4-(4-Fluorophenyl)-6-tosylhexahydropyrrolo[3,4-e][1,3]oxazin-2(3H)-one (Ig);
tert-Butyl ((R)-furan-2-yl((3R,4S)-4-hydroxy-1tosylpyrrolidin-3-yl)methyl)carbamate (Ih);
tert-Butyl ((R)-((3R,4S)-4-hydroxy-1-tosylpyrrolidin-3-yl)(4-(methylthio)phenyl)methyl)carbamate (Ii);
tert-Butyl ((R)-((3R,4S)-4-hydroxy-1-tosylpyrrolidin-3-yl)(thiophen-2-yl)methyl)carbamate (Ij);
tert-Butyl ((R)-((3R,4S)-4-hydroxy-1-tosylpyrrolidin-3-yl)(4-methoxyphenyl)methyl)carbamate (Ik);
ethyl (2S,3R,4R)-4-((R)-((tert-butoxycarbonyl)amino)(phenyl)methyl)-3-(2ethoxy-2-oxoethyl)-1-tosylpyrrolidine-2-carboxylate (IA);
ethyl (2S,3R,4R)-4-((R)-((tert-butoxycarbonyl)amino)(4chlorophenyl)methyl)-3-(2-ethoxy-2-oxoethyl)-1-tosylpyrrolidine-2carboxylate (IB);
ethyl (2S,3R,4R)-4-((R)-((tert-butoxycarbonyl)amino)(4-(trifluoromethyl)phenyl)methyl)-3-(2-ethoxy-2-oxoethyl)-1-tosylpyrrolidine-2-carboxylate (IC);
ethyl (2S,3R,4R)-4-((R)-((tert-butoxycarbonyl)amino)(p-tolyl)methyl)-3-(2-ethoxy-2-oxoethyl)-1-tosylpyrrolidine-2-carboxylate (ID);
ethyl (2S,3R,4R)-4-((R)-((tert-butoxycarbonyl)amino)(naphthalen-2-yl)methyl)-3-(2-ethoxy-2-oxoethyl)-1-tosylpyrrolidine-2-carboxylate (IE);
ethyl (2S,3R,4R)-4-((R)-(4-bromophenyl)((tert-butoxycarbonyl)amino)methyl)-3-(2-ethoxy-2-oxoethyl)-1-tosylpyrrolidine-2-carboxylate (IF);
ethyl (2S,3R,4R)-4-((R)-((tert-butoxycarbonyl)amino)(4-fluorophenyl)methyl)-3-(2-ethoxy-2-oxoethyl)-1-tosylpyrrolidine-2-carboxylate (IG);
ethyl (2S,3R,4R)-4-((R)-((tert-butoxycarbonyl)amino)(furan-2-yl)methyl)-3-(2-ethoxy-2-oxoethyl)-1-tosylpyrrolidine-2-carboxylate (IH);
Diisopropyl (3R,4S)-3-benzyl-4-(2-ethoxy-2-oxoethyl)pyrazolidine-1,2-dicarboxylate (2a);
Diethyl (3R,4S)-3-benzyl-4-(2-ethoxy-2-oxoethyl)pyrazolidine-1,2-dicarboxylate (2b);
Di-tert-butyl (3R,4S)-3-benzyl-4-(2-ethoxy-2-oxoethyl)pyrazolidine-1,2-dicarboxylate (2c);
diisopropyl (3R,4S)-4-(2-ethoxy-2-oxoethyl)-3-(naphthalen-2-ylmethyl)pyrazolidine-1,2-dicarboxylate (2d);
Diisopropyl (3R,4S)-4-(2-ethoxy-2-oxoethyl)-3-(4-methoxybenzyl)pyrazolidine-1,2-dicarboxylate (2e);
diisopropyl (3R,4S)-3-(3-(benzyloxy)propyl)-4-(2-ethoxy-2-oxoethyl)pyrazolidine-1,2-dicarboxylate (2f);
Diisopropyl (3R,4S)-4-(2-ethoxy-2-oxoethyl)-3-(4-(methylthio)benzyl)pyrazolidine-1,2-dicarboxylate (2g);
Diisopropyl (3R,4S)-4-(2-ethoxy-2-oxoethyl)-3-(4-methylbenzyl)pyrazolidine-1,2-dicarboxylate (2h);
Diisopropyl (3R,4S)-4-(2-ethoxy-2-oxoethyl)-3-((6-nitrobenzo[d][1,3]dioxol-5-yl)methyl)pyrazolidine-1,2-dicarboxylate (2i);
di-tert-butyl (3R,4S)-4-(2-ethoxy-2-oxoethyl)-3-((6-nitrobenzo[d][1,3]dioxol-5-yl)methyl)pyrazolidine-1,2-dicarboxylate (2j);
Diisopropyl (3R,4S)-3-((6-cyanobenzo[d][1,3]dioxol-5-yl)methyl)-4-(2-ethoxy-2-oxoethyl)pyrazolidine-1,2-dicarboxylate (2k);
Diisopropyl (3R,4S)-4-(2-ethoxy-2-oxoethyl)-3-methylpyrazolidine-1,2-dicarboxylate (2l); and
Diisopropyl (3R,4S)-4-(2-ethoxy-2-oxoethyl)-3-propylpyrazolidine-1,2-dicarboxylate (2m).

3. A process for the synthesis of a novel substituted 5 membered heterocyclic compounds of Formula I according to claim 1, with >80% ee (80-100) and with >60 (60-85) % yield, wherein the said process comprises the steps of:
  a. dissolving N-Boc-protected imine IIa-k in anhydrous acetonitrile and adding the β-amino aldehyde III to obtain a mixture;
  b. cooling the mixture of step (a) and adding proline followed by addition of ethyl 2-(triphenyl-15-phosphanylidene)acetate, ethyl bromo acetate, Cs$_2$CO$_3$ and heating the reaction mixture;
  c. cooling the mixture of step (a) and adding -proline followed by addition of a solution of CH$_2$=SOMe$_2$ in DMSO/THF; and d. quenching and work-up of the reaction mixture of step (b) or step (c) affords a pure product IA-H or Ia-k.

4. A process for the synthesis of a novel substituted 5 membered heterocyclic compounds of Formula 2a to 2m according to claim 2 from aldehydes of Formula IVa' to IVj' comprising:
   a. adding aldehyde of Formula 1Va' to 1Vj' to a solution of diisopropyl azodicarboxylate (DIAD) and proline (10 mol %) in $CH_3CN$ and stirring to obtain a mixture;
   b. adding ethyl 2-(triphenyl-15-phosphanylidene) acetate to the mixture of step (a) and stirring the reaction mixture followed by addition of Corey-Chaykovsky reagent to complete the reaction; and
   c. quenching followed by workup affords the pure products 2a-2m.

5. The process as claimed in claim 3, wherein said proline is selected from (L)-proline or D-proline.

6. The process as claimed in claim 4, wherein said proline is selected from (L)-proline or D-proline.

7. A method for treating mycobacterial infection in a subject in need thereof, comprising administering to the subject a therapeutically effective amount of a compound according to claim 1 or a pharmaceutically acceptable salt thereof.

* * * * *